(12) United States Patent
Woodard, Jr. et al.

(10) Patent No.: US 8,906,043 B2
(45) Date of Patent: Dec. 9, 2014

(54) LAPAROSCOPIC SUTURING INSTRUMENT WITH PERPENDICULAR ECCENTRIC NEEDLE MOTION

(75) Inventors: James A. Woodard, Jr., Mason, OH (US); Jason R. Lesko, Harrison, OH (US); Shawn C. Snyder, Greendale, IN (US); David T. Martin, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 367 days.

(21) Appl. No.: 13/295,210

(22) Filed: Nov. 14, 2011

(65) Prior Publication Data

US 2012/0143223 A1 Jun. 7, 2012

Related U.S. Application Data

(60) Provisional application No. 61/413,696, filed on Nov. 15, 2010.

(51) Int. Cl.
*A61B 17/04* (2006.01)
*A61B 17/29* (2006.01)
*A61B 17/06* (2006.01)
*A61B 17/062* (2006.01)

(52) U.S. Cl.
CPC ..... *A61B 17/0469* (2013.01); *A61B 2017/2903* (2013.01); *A61B 2017/2944* (2013.01); *A61B 17/0491* (2013.01); *A61B 2017/2906* (2013.01); *A61B 2017/06047* (2013.01); *A61B 17/29* (2013.01); *A61B 17/0625* (2013.01); *A61B 17/062* (2013.01); *A61B 2017/2929* (2013.01); *A61B 2017/0609* (2013.01)
USPC ........................................................ 606/147

(58) Field of Classification Search
USPC .................. 606/147, 144, 222, 223; 112/220
See application file for complete search history.

(56) References Cited

U.S. PATENT DOCUMENTS 2,363,334 A 11/1944 Jones
5,300,082 A 4/1994 Sharpe et al.
(Continued)

FOREIGN PATENT DOCUMENTS

WO WO 98/48705 11/1998
WO WO 98/57585 11/1998
(Continued)

OTHER PUBLICATIONS

U.S. Appl. No. 13/156,420, filed Jun. 9, 2011, Woodard, Jr. et al.
(Continued)

*Primary Examiner* — Thomas McEvoy
*Assistant Examiner* — Julie A Szpira
(74) *Attorney, Agent, or Firm* — Frost Brown Todd LLC

(57) ABSTRACT

A suture needle driving instrument comprises a shaft and an end effector. The end effector is located at the distal end of the shaft and includes a pair of needle grasping arms. Each grasping arm extends along a respective arm axis. The grasping arms are operable to drive a suture needle along a rotational path about an axis, such as one of the arm axes, that is offset from the central longitudinal axis of the shaft. The rotational path may be perpendicular to the axis of the shaft. A needle driven by the end effector may have an arc radius that is greater than the radius of the shaft. At least one of the needle grasping arms may include a dogleg feature positioning a distal portion of the grasping arm outside the radius of the shaft. The instrument may be used through a trocar during minimally invasive surgery.

18 Claims, 25 Drawing Sheets

(56) References Cited

U.S. PATENT DOCUMENTS

| | | | |
|---|---|---|---|
| 5,582,617 A * | 12/1996 | Klieman et al. | 606/170 |
| 5,897,563 A | 4/1999 | Yoon et al. | |
| 5,954,733 A | 9/1999 | Yoon | |
| 5,957,937 A | 9/1999 | Yoon | |
| 5,984,932 A | 11/1999 | Yoon | |
| 6,004,332 A | 12/1999 | Yoon et al. | |
| 6,056,771 A | 5/2000 | Proto | |
| 6,071,289 A | 6/2000 | Stefanchik et al. | |
| 6,159,224 A | 12/2000 | Yoon | |
| 6,206,894 B1 * | 3/2001 | Thompson et al. | 606/144 |
| 6,224,614 B1 * | 5/2001 | Yoon | 606/147 |
| 6,905,498 B2 | 6/2005 | Hooven | |
| 7,628,796 B2 | 12/2009 | Shelton, IV et al. | |
| 7,785,335 B2 | 8/2010 | Otten | |
| 8,137,339 B2 | 3/2012 | Jinno et al. | |
| 2004/0068274 A1 | 4/2004 | Hooven | |
| 2006/0064115 A1 | 3/2006 | Allen et al. | |
| 2008/0306495 A1 | 12/2008 | Thompson et al. | |
| 2010/0100125 A1 | 4/2010 | Mahadevan | |
| 2012/0123471 A1 | 5/2012 | Woodard, Jr. et al. | |
| 2012/0143223 A1 | 6/2012 | Woodard, Jr. et al. | |

FOREIGN PATENT DOCUMENTS

| | | |
|---|---|---|
| WO | WO 99/05974 | 2/1999 |
| WO | WO 99/55217 | 11/1999 |
| WO | WO 99/65398 | 12/1999 |

OTHER PUBLICATIONS

U.S. Appl. No. 13/295,186, filed Nov. 14, 2011, Woodard, Jr. et al.
International Search Report and Written Opinion dated Feb. 13, 2012 for Application No. PCT/US2011/060572.
International Search Report and Written Opinion dated Feb. 3, 2012 for Application No. PCT/US2011/060574.

\* cited by examiner

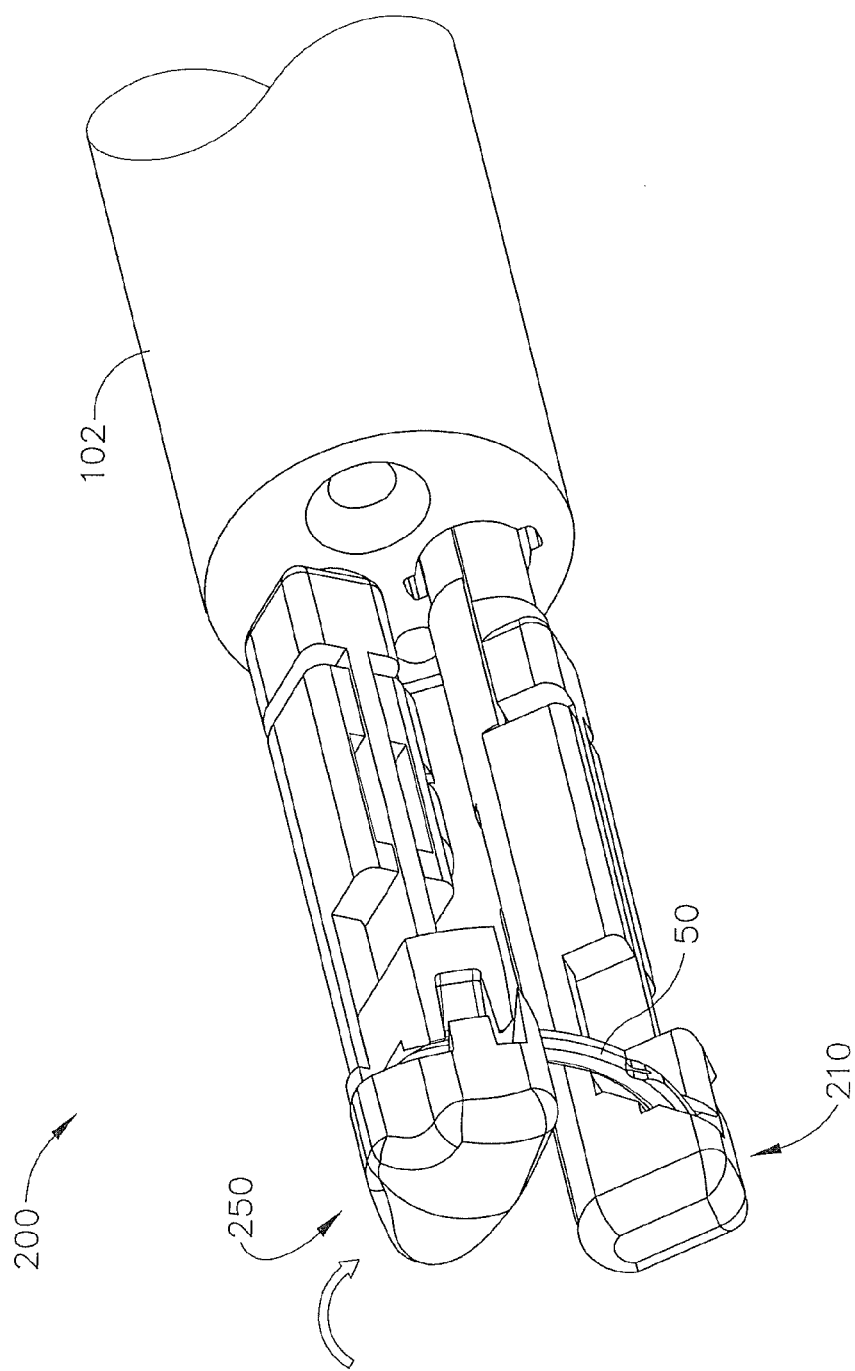

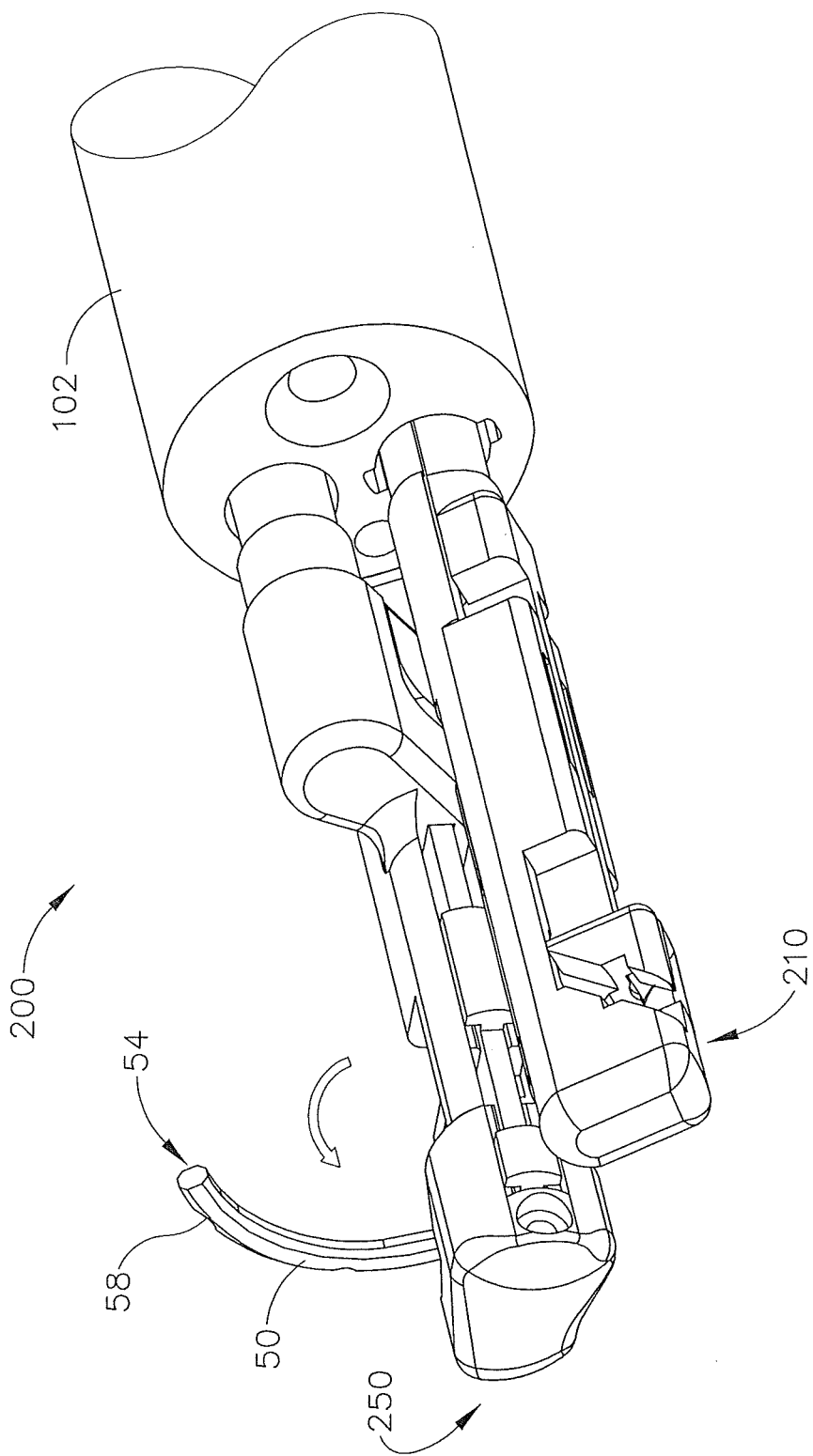

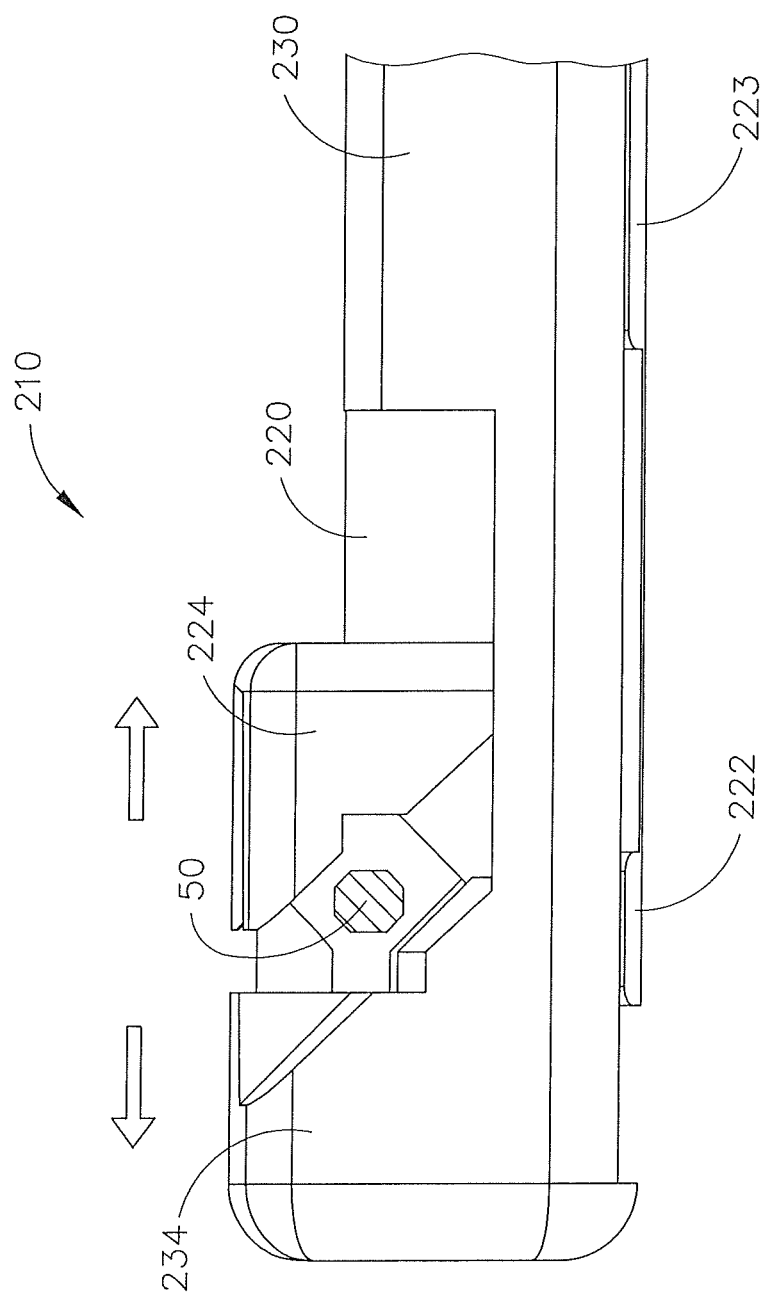

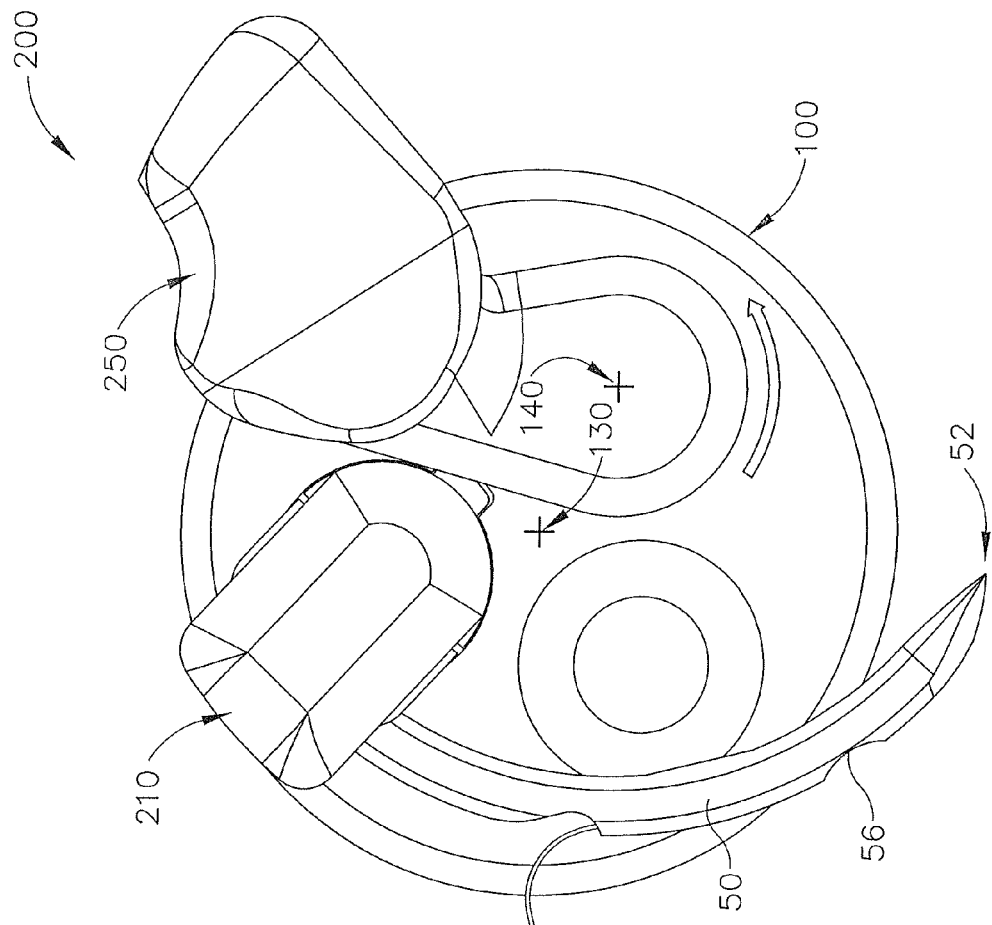
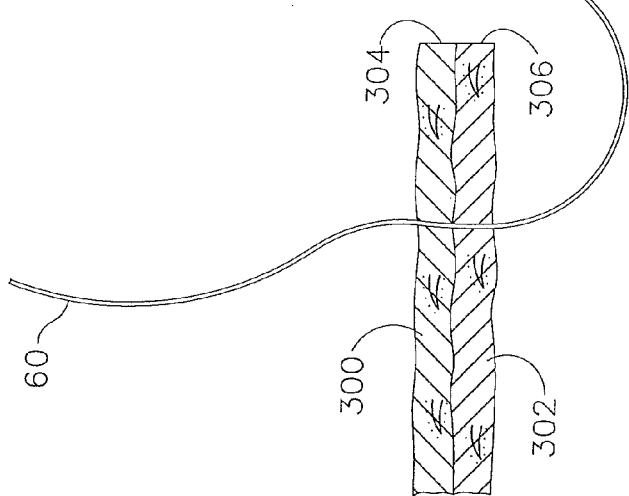
Fig.12G

LAPAROSCOPIC SUTURING INSTRUMENT WITH PERPENDICULAR ECCENTRIC NEEDLE MOTION

PRIORITY

This application claims priority to U.S. Provisional Application Ser. No. 61/413,696, filed Nov. 15, 2010, entitled "Perpendicular Architecture Gen II," the disclosure of which is incorporated by reference herein.

BACKGROUND

In some settings it may be desirable to perform a surgical procedure in a minimally invasive manner, such as through a trocar or other type of access cannula. Examples of trocars include the various ENDOPATH® EXCEL™ products by Ethicon Endo-Surgery, Inc. of Cincinnati, Ohio. Such trocars may present different inner diameters, such as those ranging from approximately 4.7 mm to approximately 12.9 mm, allowing a surgeon to choose a particular trocar based on a balance of considerations such as access needs and incision size. In some minimally invasive surgical procedures, at least two trocars may be inserted through the abdominal wall of the patient. An imaging device such as an endoscope may be inserted through one of the trocars to provide visualization of the surgical site. A surgical instrument may be inserted through another one of the trocars to perform surgery at the site. In procedures performed within the abdominal cavity, the cavity may be insufflated with pressurized carbon dioxide to provide more room for visualization and manipulation of instruments. In some settings, additional trocars may be used to provide access for additional surgical instruments. Minimally invasive surgery may also be performed through access portals such as the Single Site Laparoscopy Access System by Ethicon Endo-Surgery, Inc. of Cincinnati, Ohio, which provides ports for more than one surgical instrument through a single incision in a patient.

It may also be desirable to use sutures during some minimally invasive surgical procedures, such as to close an opening, to secure two layers of tissue together, to provide an anastomosis, etc. Such use of sutures may be in addition to or in lieu of using other devices and techniques such as clips, staples, electrosurgical sealing, etc. Performing suturing through trocars or other minimally invasive access ports may be more difficult than suturing in an open surgical procedure. For instance, manipulating a needle and suture with conventional tissue graspers through trocars may be relatively difficult for many surgeons. Thus, improved laparascopic surgical instruments may make suturing procedures performed through trocars relatively easier. Examples of surgical instruments configured to facilitate suturing through trocars include the LAPRA-TY® Suture Clip Applier, the Suture Assistant, and the ENDOPATH® Needle Holder, all of which are by Ethicon Endo-Surgery, Inc. of Cincinnati, Ohio. Additional suturing instruments are disclosed in U.S. Pat. No. 7,628,796, entitled "Surgical Suturing Apparatus with Anti-Backup System," issued Dec. 8, 2009, the disclosure of which is incorporated by reference herein; U.S. Pat. No. 6,071,289, entitled "Surgical Device for Suturing Tissue," issued Jun. 6, 2000, the disclosure of which is incorporated by reference herein; U.S. patent application Ser. No. 13/156,420, entitled "Laparoscopic Suture Device with Asynchronous In-Line Needle Movement," filed Jun. 9, 2011, and published Dec. 22, 2011 as U.S. Pub. No. 2011/0313433, the disclosure of which is incorporated by reference herein; and U.S. Provisional Patent Application No. 61/355,832, entitled "Laparoscopic Suture Device," filed Jun. 17, 2010, the disclosure of which is incorporated by reference herein.

Exemplary suturing needles are disclosed in U.S. Pat. No. 6,056,771, entitled "Radiused Tip Surgical Needles and Surgical Incision Members," issued May 2, 2000, the disclosure of which is incorporated by reference herein; U.S. Pub. No. 2010/0100125, entitled "Suture Needle and Suture Assembly," published Apr. 22, 2010, the disclosure of which is incorporated by reference herein; U.S. Provisional Application Ser. No. 61/413,680, filed Nov. 15, 2010, entitled "Custom Needle for Suture Instrument," the disclosure of which is incorporated by reference herein; and U.S. patent application Ser. No. 13/295,186, entitled "Needle for Laparoscopic Suturing Instrument," filed on even date herewith, and published May 17, 2012 as U.S. Pub. No. 2012/0123471, the disclosure of which is incorporated by reference herein.

While a variety of devices and methods have been made and used for suturing tissue, it is believed that no one prior to the inventor(s) has made or used the technology described herein.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 3B depicts a perspective view of the end effector and needle of FIG. 3A, in a second operational configuration;

FIG. 3C depicts a perspective view of the end effector and needle of FIG. 3A, in a third operational configuration;

FIG. 6A depicts a partial side elevational view of the first needle grasping arm of FIG. 4, in a first operational configuration;

FIG. 12G depicts an end view of the end effector and needle of FIG. 3A, during an exemplary seventh stage of operation;

Figure 1:
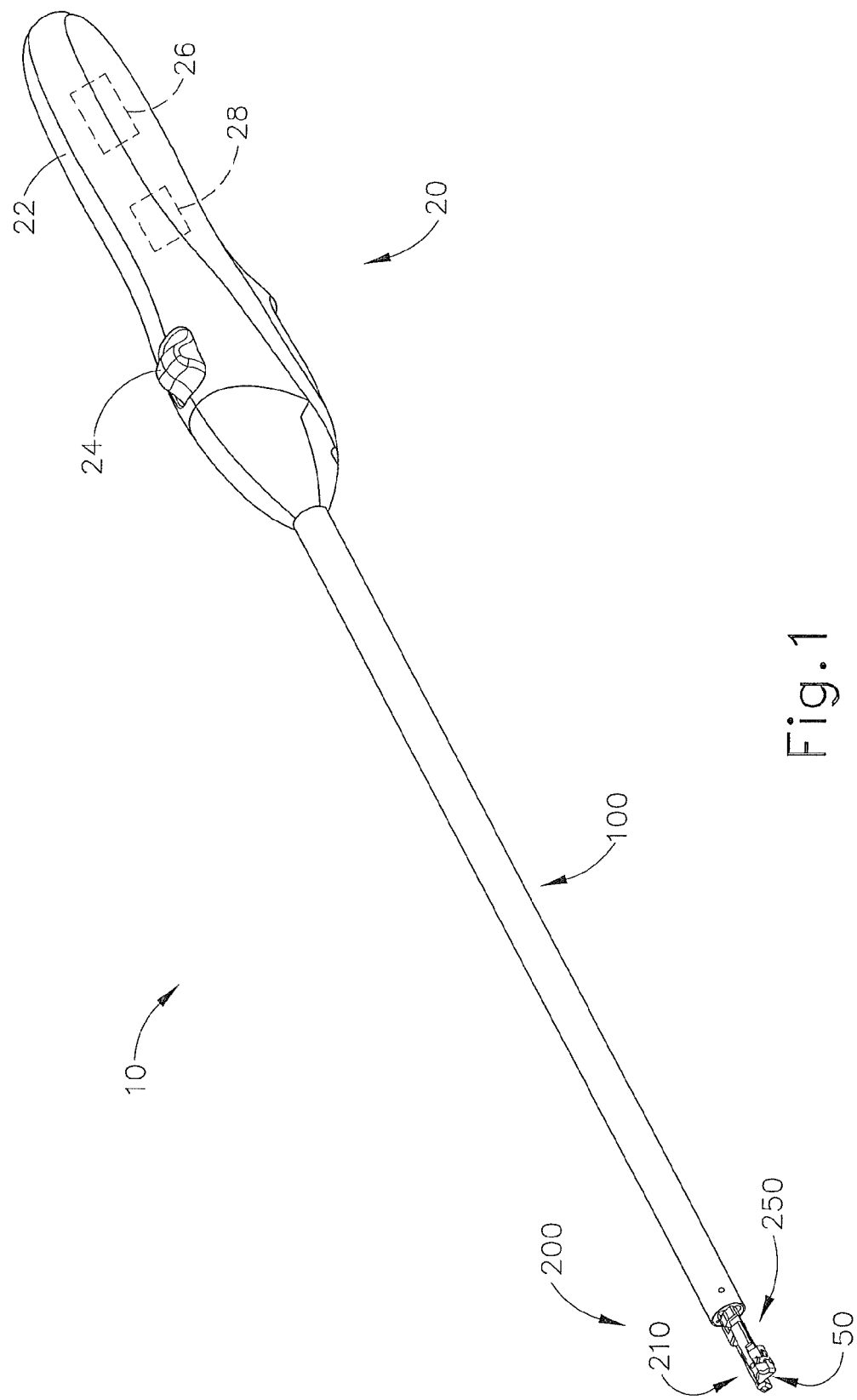
FIG. 1 depicts a perspective view of an exemplary laparoscopic suturing instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It should therefore be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview

FIG. 1 shows an exemplary laparoscopic suturing instrument (10). Instrument (10) of this example includes a handle portion (20), a shaft (100) extending distally from handle portion (20), and an end effector (200) at the distal end of shaft (100). Handle portion (20) includes a grip (22), a rocker (24), an integral power source (26), and a motor (28) in communication with the integral power source (26). Rocker (24) is resiliently biased to a generally vertical position (e.g., generally perpendicular to grip (22)), though rocker (24) may be rocked forwardly or rearwardly. In addition or in the alternative, rocker (24) may be rocked to the left or to the right. Rocker (24) is operable to actuate features of end effector (200) as will be described in greater detail below. Of course, rocker (24) is merely one example of a user input feature, and any other suitable type of user input feature may be used.

Integral power source (26) comprises a rechargeable battery in the present example, though it should be understood that any other suitable power source may be used. By way of example only, instrument (10) may use a power source that is external to instrument (10) (e.g., coupled with instrument (10) via a cable, etc.). Similarly, while end effector (200) is powered by motor (28) in the present example, it should be understood that any other suitable source may be used, including but not limited to a manually operable mechanism. Various other suitable components, features, and configurations for handle portion (20) will be apparent to those of ordinary skill in the art in view of the teachings herein. By way of example only, handle portion (20) may be constructed in accordance with at least some of the teachings of U.S. Provisional Patent Application No. 61/355,832, the disclosure of which is incorporated by reference herein; and/or in accordance with at least some of the teachings of U.S. patent application Ser. No. 13/156,420, published as U.S. Pub. No. 2011/0313433, the disclosure of which is incorporated by reference herein.

Shaft (100) of the present example has an outer diameter sized to permit shaft (100) to be inserted through a conventional trocar (not shown). Shaft (100) also has a length sized to permit end effector (200) to be positioned at a surgical site within a patient while also allowing handle portion (20) to be manipulated by a user (e.g., a surgeon) from a location outside the patient when shaft (100) is disposed in a trocar. Of course, shaft (100) need not necessarily be dimensioned for use through a trocar. For instance, instrument (10) may be used and/or configured for use in open surgical procedures.

In some versions, shaft (100) includes one or more articulating features, allowing end effector (200) to be articulated to various angles and positions relative to the longitudinal axis defined by shaft (100). Merely illustrative examples of such articulation are taught in U.S. Provisional Application Ser. No. 61/355,832, the disclosure of which is incorporated by reference herein. Various other suitable ways in which articulation may be provided will be apparent to those of ordinary skill in the art in view of the teachings herein. In addition or in the alternative, shaft (100) may be rotatable about the longitudinal axis, relative to handle portion (20), to selectively position end effector (200) at various angular orientations about the longitudinal axis. Of course, a user may rotate the entire instrument (10) about the longitudinal axis to selectively position end effector (200) at various angular orientations about the longitudinal axis.

End effector (200) of the present example includes a first grasping arm (210) and a second grasping arm (250). As will be described in greater detail below, arms (210, 250) are configured to alternatingly throw and catch a curved suturing needle (50) along a path/plane that is substantially perpendicular to the longitudinal axis defined by shaft (100). Alternatively, arms (210, 250) may be configured to alternatingly throw and catch needle (50) along a path that is substantially parallel to the longitudinal axis defined by shaft (100); or along some other path.

In some versions, arms (210, 250) pass needle (50) back and forth from arm (42) to arm (210) and from arm (250) to arm (210) in an oscillating motion (i.e., back and forth in opposite directions), such that needle (50) does not traverse a circular path as needle (50) is being passed between arms (210, 250). Such action of needle (50) may be referred to as a "reverse reset." In some other versions, needle (50) may be passed between arms (210, 250) along a circular path in a single direction. Such action of needle (50) may be referred to as a "forward reset." By way of example only, arms (210, 250) may move in accordance with at least some of the teachings of U.S. Provisional Patent Application No. 61/355,832, the disclosure of which is incorporated by reference herein; and/or in accordance with at least some of the teachings of U.S. patent application Ser. No. 13/156,420, published as U.S. Pub. No. 2011/0313433, the disclosure of which is incorporated by reference herein. Regardless of whether arms (210, 250) move synchronously or asynchronously, arms (210, 250) may be configured to grip and/or compress tissue that is positioned between arms (210, 250) when arms are in approximated positions, which may facilitate passage of needle (50) through the tissue.

Figure 2:
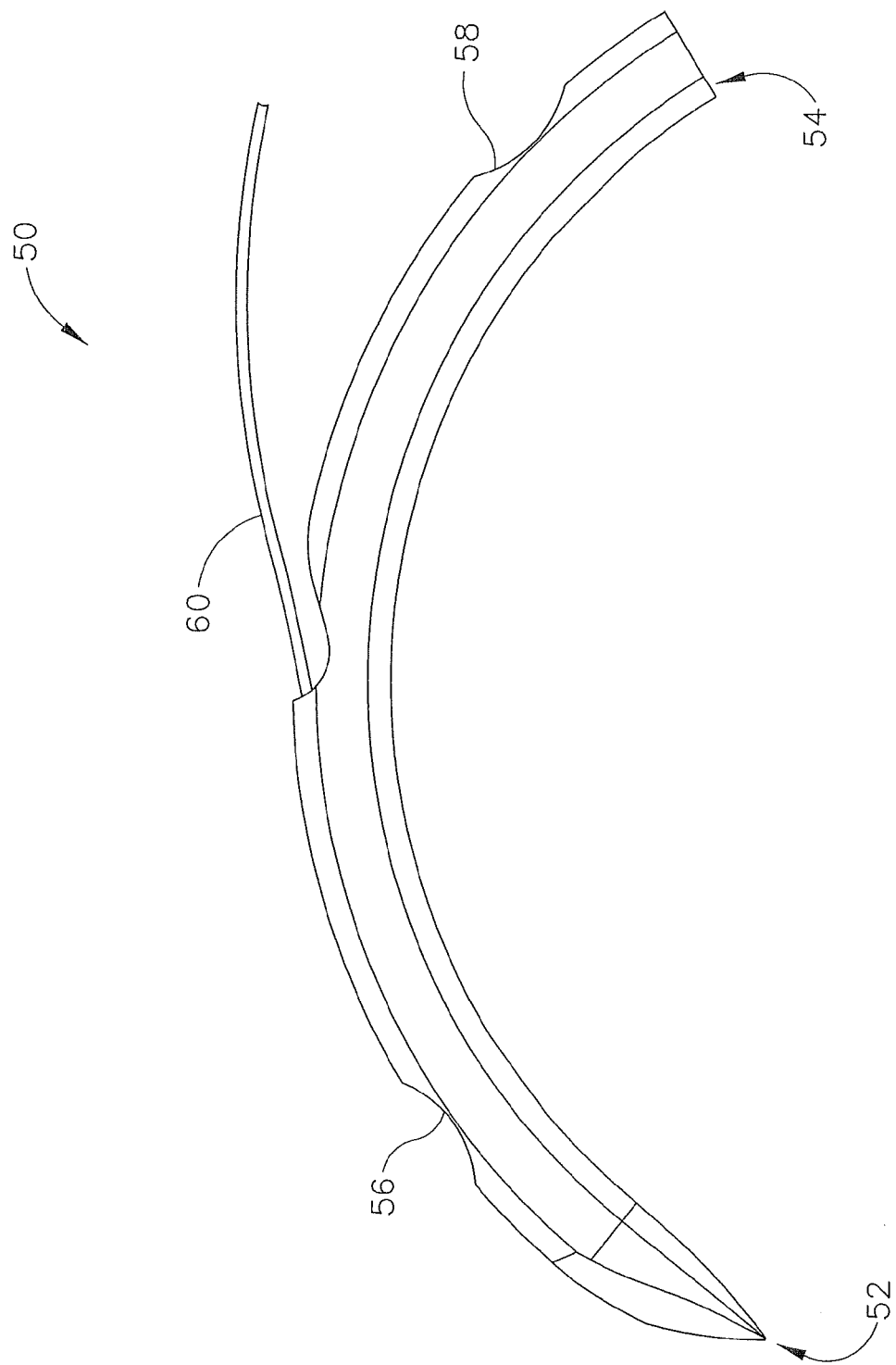
FIG. 2 depicts a side elevational view of an exemplary laparoscopic suturing needle for use with the suturing instrument of FIG. 1.

FIG. 2 shows needle (50) in greater detail. Needle (50) of this example includes a sharp tip (52), a blunt end (54), and a pair of grasping regions (56, 58) configured for grasping by arms (210, 250). In particular, grasping regions (56, 58) comprise scallops in the present example, though it should be understood that grasping regions (56, 58) may have various other configurations. A suture (60) is secured to a mid-region of needle (50). The configuration and relationship of suture (60) and needle (50) provides an exit of suture (60) from needle (50) at an angle that is generally tangent to or oblique relative to the curvature of needle (50). Such an angle may provide reduced drag forces and/or reduced tissue trauma as compared to drag forces and/or tissue trauma that might otherwise be encountered using a needle with a suture that exits at a generally perpendicular angle.

While the example described below includes just a single strand of suture extending from the needle, it should be understood that two or more strands may extend from the needle (e.g., double leg suture, etc.). As yet another merely illustrative example, suture (60) may be secured to blunt end (54) of needle (50) instead of being secured to a mid-region of needle (50). In still other versions, end (54) includes a sharp tip instead of being blunt. It should also be understood that needle (50) may be straight instead of curved in some versions. By way of example only, needle (50) may be constructed in accordance with at least some of the teachings of U.S. Provisional Application Ser. No. 61/413,680; U.S. patent application Ser. No. 13/295,186, published as U.S. Pub. No. 2012/0123471; U.S. Pat. No. 6,056,771; and/or U.S. Pub. No. 2010/0100125. Still other suitable configurations for needle (50) will be apparent to those of ordinary skill in the art in view of the teachings herein.

It should also be understood that needle (50) may be constructed using various techniques. By way of example only, needle (50) may be constructed using metal-injection-molding (MIM) processes. Needle (50) may also be formed from a sheet, wire, tube, extrusion, or other components that are bent, stamped, coined, milled, otherwise machined, and/or otherwise formed. Other suitable ways in which needle (50) may be constructed will be apparent to those of ordinary skill in the art in view of the teachings herein.

II. Exemplary End Effector

As noted above, end effector (200) comprises a pair of grasping arms (210, 250) that are operable to selectively grasp needle (50) during a suturing procedure. Grasping arms (210, 250) are exposed relative to an endcap (102) of shaft (100). Each grasping arm (210, 250) extends along a respective axis that is parallel to yet offset from the center axis of shaft (100). First grasping arm (210) maintains a fixed rotational position relative to shaft (100) during operation of instrument (10) in the present example. In some other versions, first grasping arm (210) is rotatable about its own longitudinal axis, relative to shaft (100). Second grasping arm (250) of the present example is rotatable about its longitudinal axis. Such motion can be seen in the series shown by FIGS. 3A-3C.

Figure 3A:
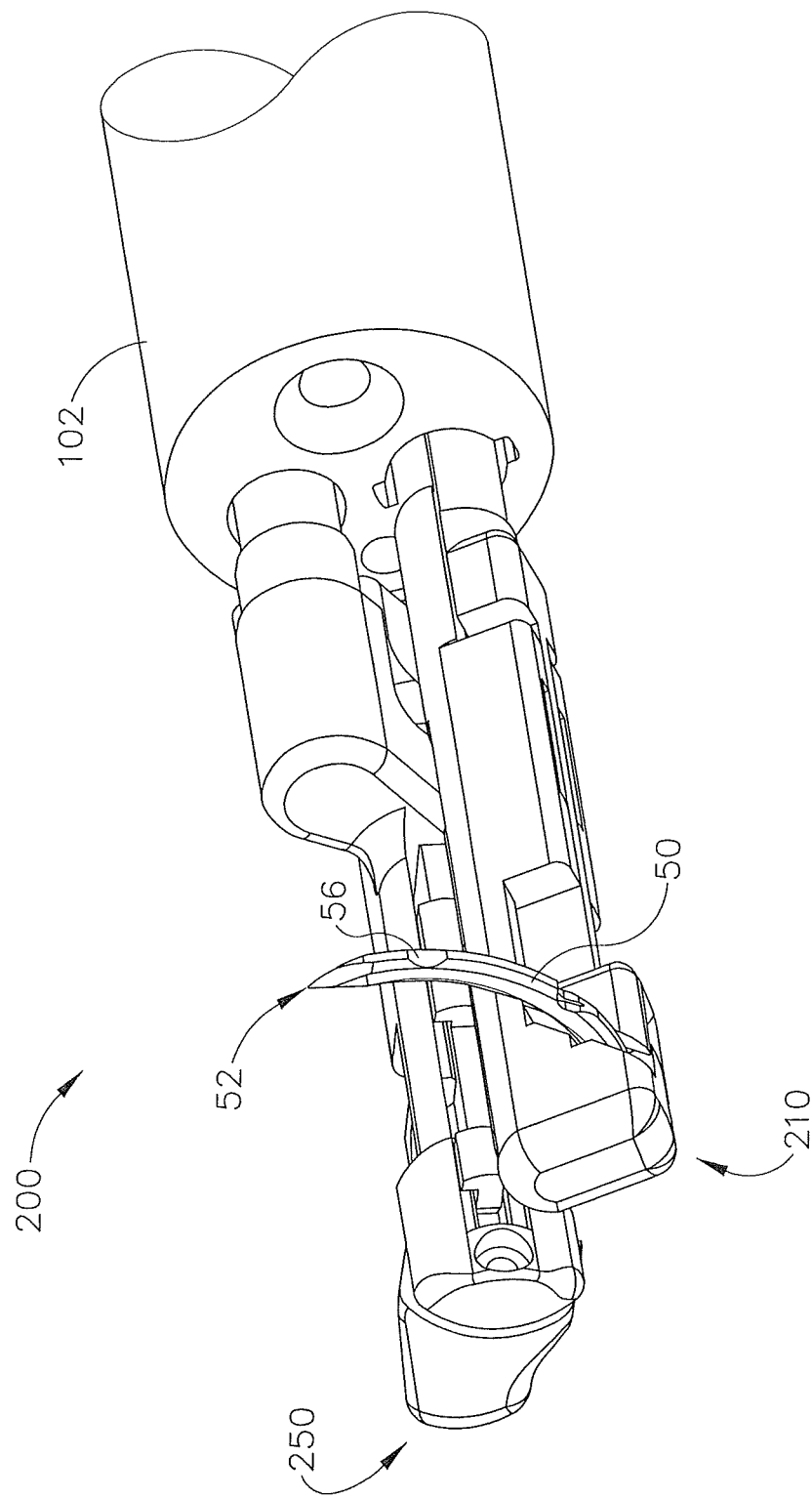
FIG. 3A depicts a perspective view of the end effector of the suturing instrument of FIG. 1 with the needle of FIG. 2, in a first operational configuration.
Figure 4:
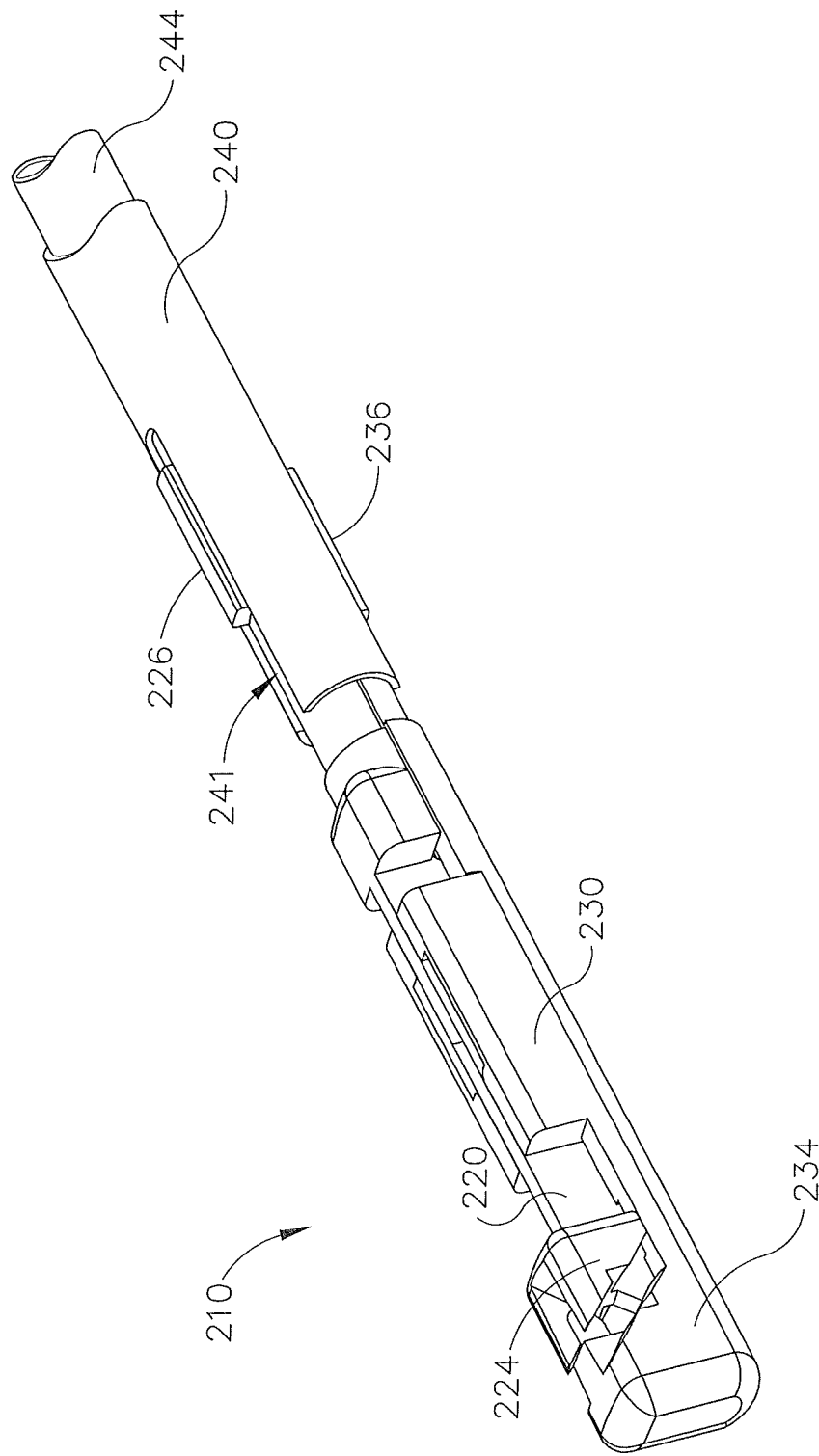
FIG. 4 depicts a first partial perspective view of a first needle grasping arm of the end effector of FIG. 3A.
Figure 5:
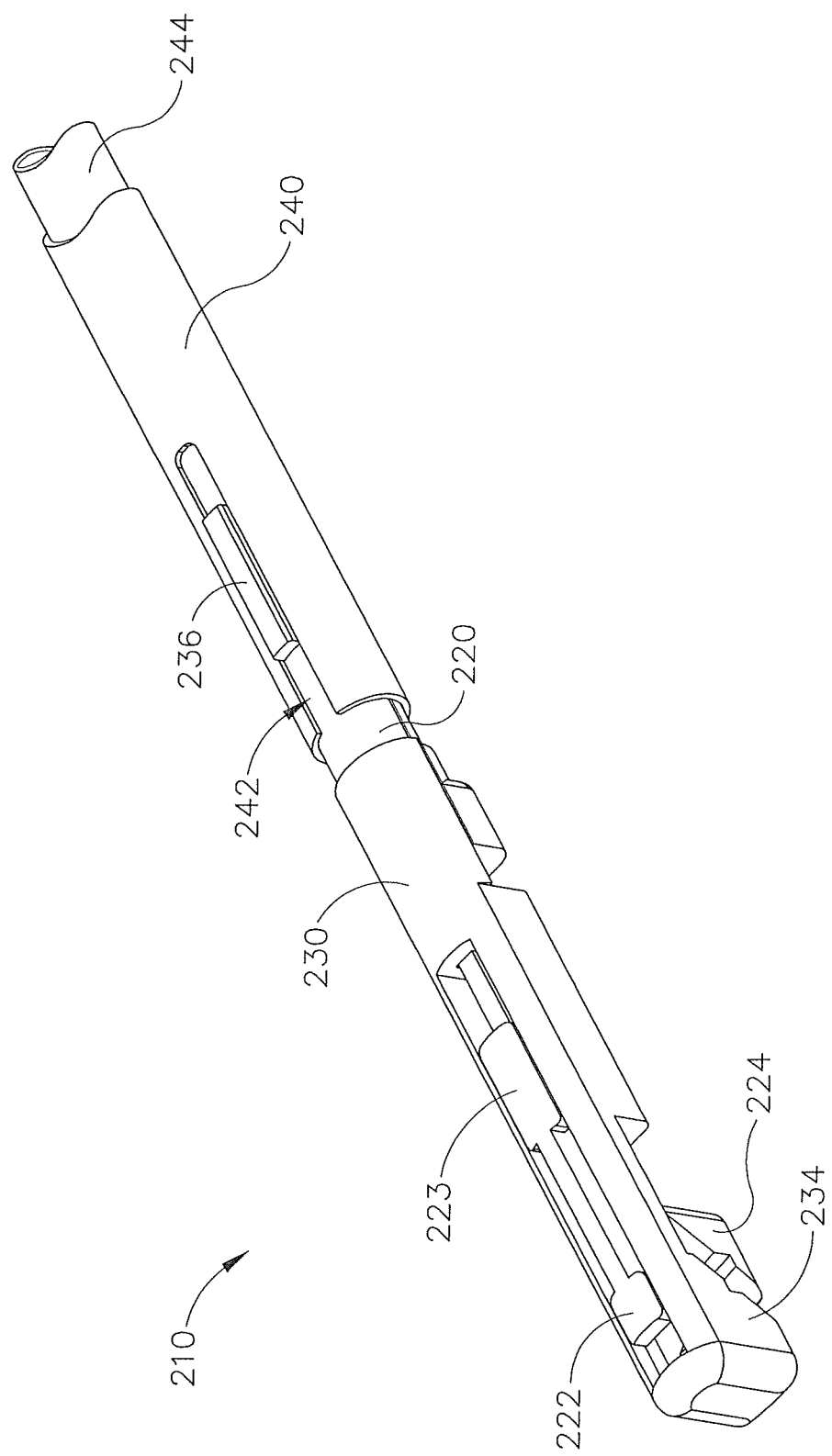
FIG. 5 depicts a second partial perspective view of the first needle grasping arm of FIG. 4.

FIG. 3A shows first grasping arm (210) grasping needle (50), with second grasping arm (250) rotated away from needle (50), exposing sharp tip (52) of needle (50). FIG. 3B shows second grasping arm (250) rotated toward needle (50) to a position enabling second grasping arm (250) to grasp needle (50) and first grasping arm (210) to release needle (50). FIG. 3C shows second grasping arm (250) rotated away from first grasping arm (210), pulling needle (50) away from second grasping arm (250). After reaching this position, second grasping arm (250) may be rotated back to the position shown in FIG. 3B, to thereby pass needle (50) back to first grasping arm (210); then rotate back to the position shown in FIG. 3A to start the cycle over again.

In the examples described herein, needle (50) is driven along a plane that is substantially perpendicular to the longitudinal axis of shaft (100). In some other examples, needle (50) is driven along a plane that is oblique relative to the longitudinal axis of shaft (100) or substantially parallel to the longitudinal axis of shaft (100). During some uses of instrument (10), needle (50) may deviate from the desired perpendicular plane. Such deviation may be due to manufacturing tolerances, deflections caused by tissue or other structures, and/or for other reasons. Such deviation may be accentuated by using a needle (50) having a relatively great length. As will be described below, end effector (200) of the present example is configured to readily accommodate and correct such off-plane deviations. In other words, arms (210, 250) are operable to grasp needle (50) even in instances where needle (50) has deviated away from the expected perpendicular plane of motion; and arms (210, 250) are further operable to redirect a deviated needle (50) back onto the expected perpendicular plane of motion.

It should be noted that suture (60) is omitted from FIGS. 3A-3C for clarity. Various components of grasping arms (210, 250) will be described in greater detail below. Various ways in which grasping arms (210, 250) may be used will also be described in greater detail below. Other suitable components of and uses for grasping arms (210, 250) will be apparent to those of ordinary skill in the art in view of the teachings herein.

A. Exemplary First Grasping Arm

FIGS. 4-7 show first grasping arm (210) in greater detail. First grasping arm (210) comprises a first jaw (220) and a second jaw (230). Jaws (220, 230) are substantially aligned with each other and are slidable longitudinally relative to each other. Jaw (220) includes a pair of flanges (222, 223) that are received through corresponding openings (232, 233) of jaw (230) during assembly of arm (210). Thereafter, flanges (222, 223) prevent jaws (220, 230) from deflecting transversely away from each other. Jaws (220, 230) also include complementary needle grasping features (224, 234) that are configured to selectively grasp needle (50) as will be described in greater detail below. The proximal portion of jaw (220) includes a transversely extending fin (226). Likewise, the proximal portion of jaw (230) also includes a transversely extending fin (236). Fins (226, 236) are slidably disposed in corresponding distal slots (241, 242) of a sheath (240). Sheath (240) extends along the length of shaft (100) and is substantially fixed within shaft (100). In particular, sheath (240) does not rotate or translate relative to shaft (100) in this example. Sheath (240) thus provides a mechanical ground in the angular direction. It should therefore be understood that the relationship between fins (226, 236) and slots (241, 242) prevent first grasping arm (210) from rotating relative to shaft (100). In some other versions, however, first grasping arm (210) is roatatable relative to shaft (100) (e.g., by rotating sheath (240) within shaft (100), etc.). It should also be understood that, in the present example, the relationship between fins (226, 236) and slots (241, 242) still permits jaws (220, 230) to translate relative to sheath (240) and shaft (100).

Figure 6B:
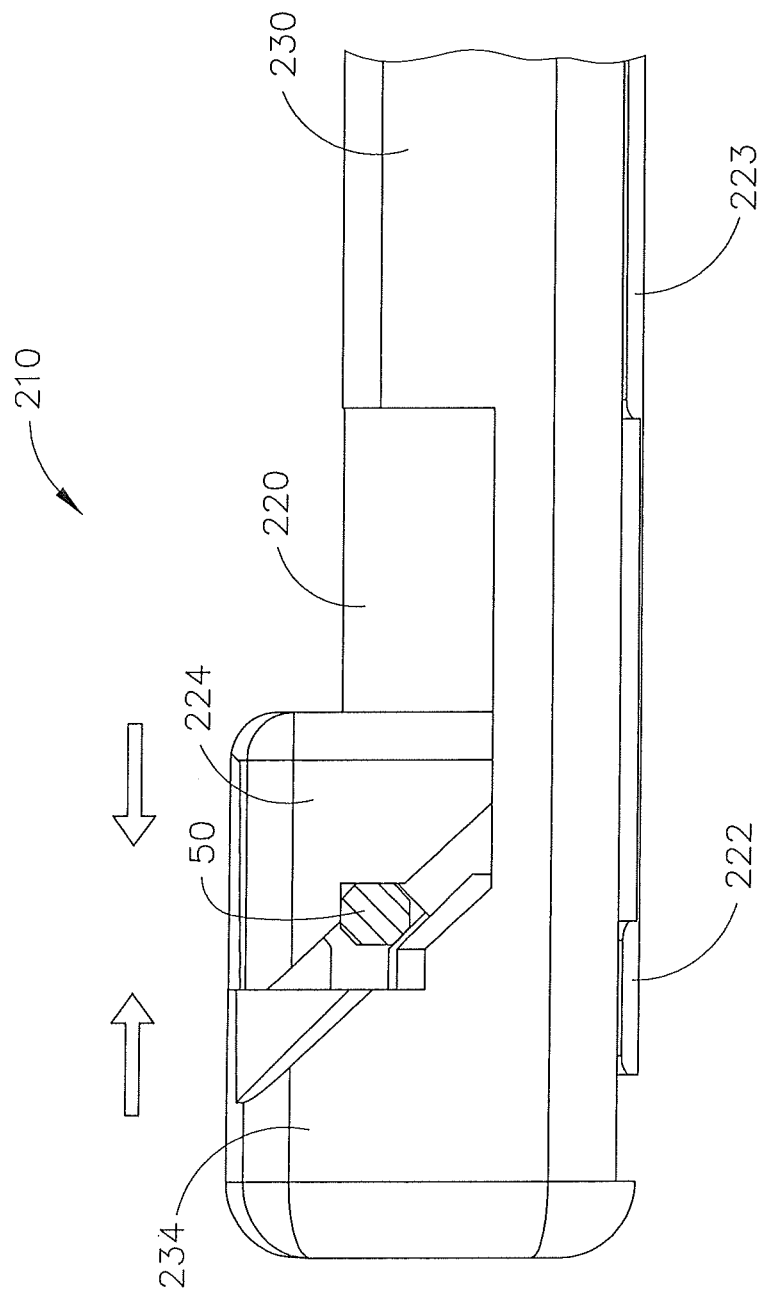
FIG. 6B depicts a partial side elevational view of the first needle grasping arm of FIG. 4, in a second operational configuration.

As best seen in FIGS. 6A-6B, jaws (220, 230) are simultaneously movable in opposite directions to selectively expand or reduce an opening formed by grasping features (224, 234) to receive needle (50). For instance, in FIG. 6A, jaw (220) has moved proximally toward shaft (100) and jaw (230) has simultaneously moved distally away from shaft (100) to enlarge the opening defined by grasping features (224, 234) to receive needle (50). In FIG. 6B, jaw (220) has moved distally away from shaft (100) and jaw (230) has simultaneously moved proximally toward shaft (100) to reduce the opening defined by grasping features (224, 234) to securely grasp needle (50). In some other versions, one jaw (220, 230) remains longitudinally stationary while the other jaw translates longitudinally to grasp or release needle (50) between grasping features (224, 234). However, it should be understood that in versions such as the present example where jaws (220, 230) both move simultaneously in opposite directions, such motion may further promote alignment of needle (50) within grasping features (224, 234) as compared to versions where one jaw (220, 230) always stays longitudinally fixed relative to shaft (100). In other words, having both grasping features (224, 234) always spaced equidistantly away from the intended path of needle (50) (regardless of whether jaws (220, 230) are open as shown in FIG. 6A or closed as shown in FIG. 6B) may better accommodate incidental deflections of needle (50) away from that intended path in either direction during use of instrument (10). Arm (210) may thus be particularly suited to accommodate instances where needle (50) has deviated away from the expected perpendicular plane of motion as described above.

Figure 7:
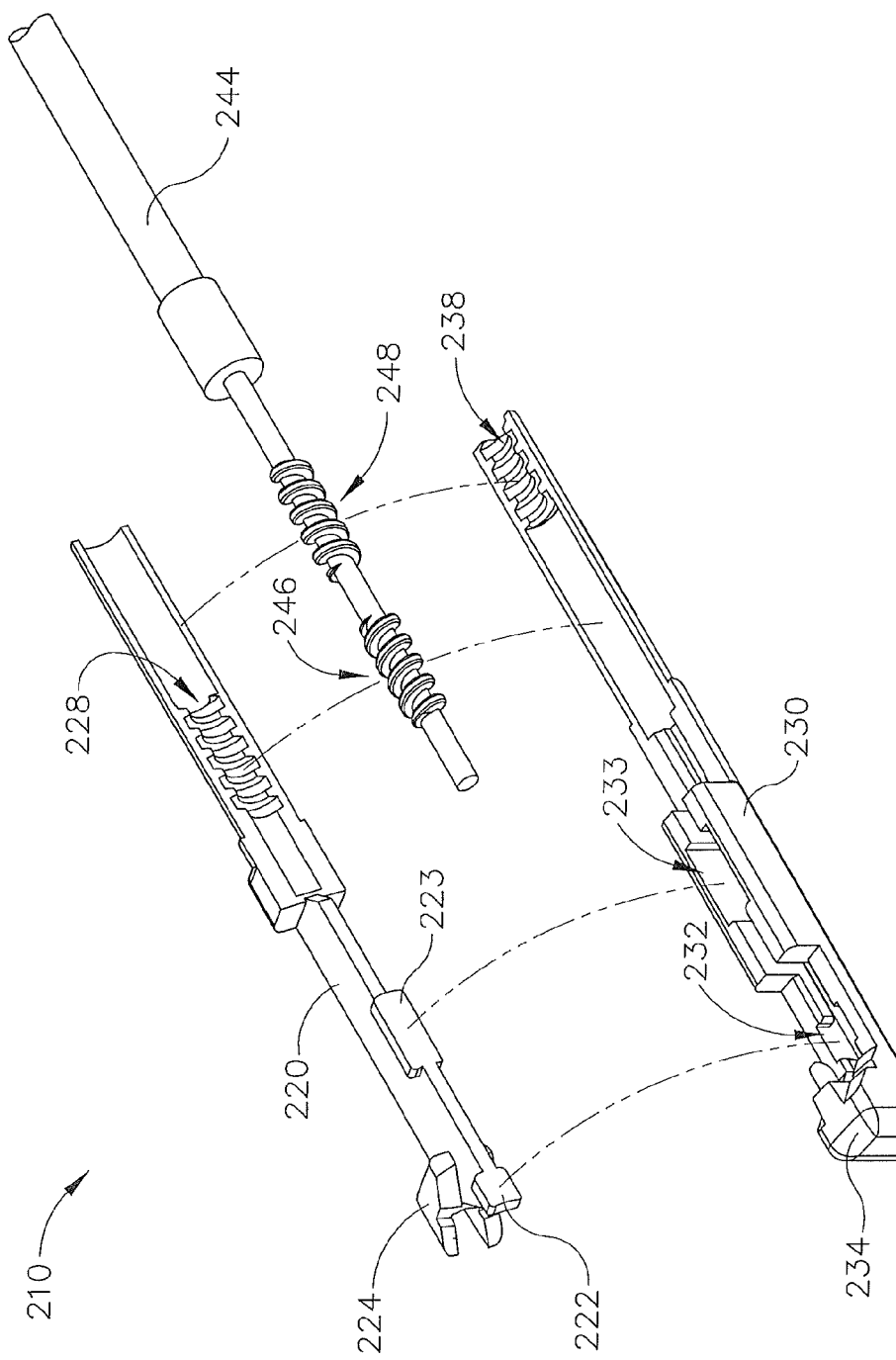
FIG. 7 depicts a partial exploded view of the first needle grasping arm of FIG. 4.
Figure 8:
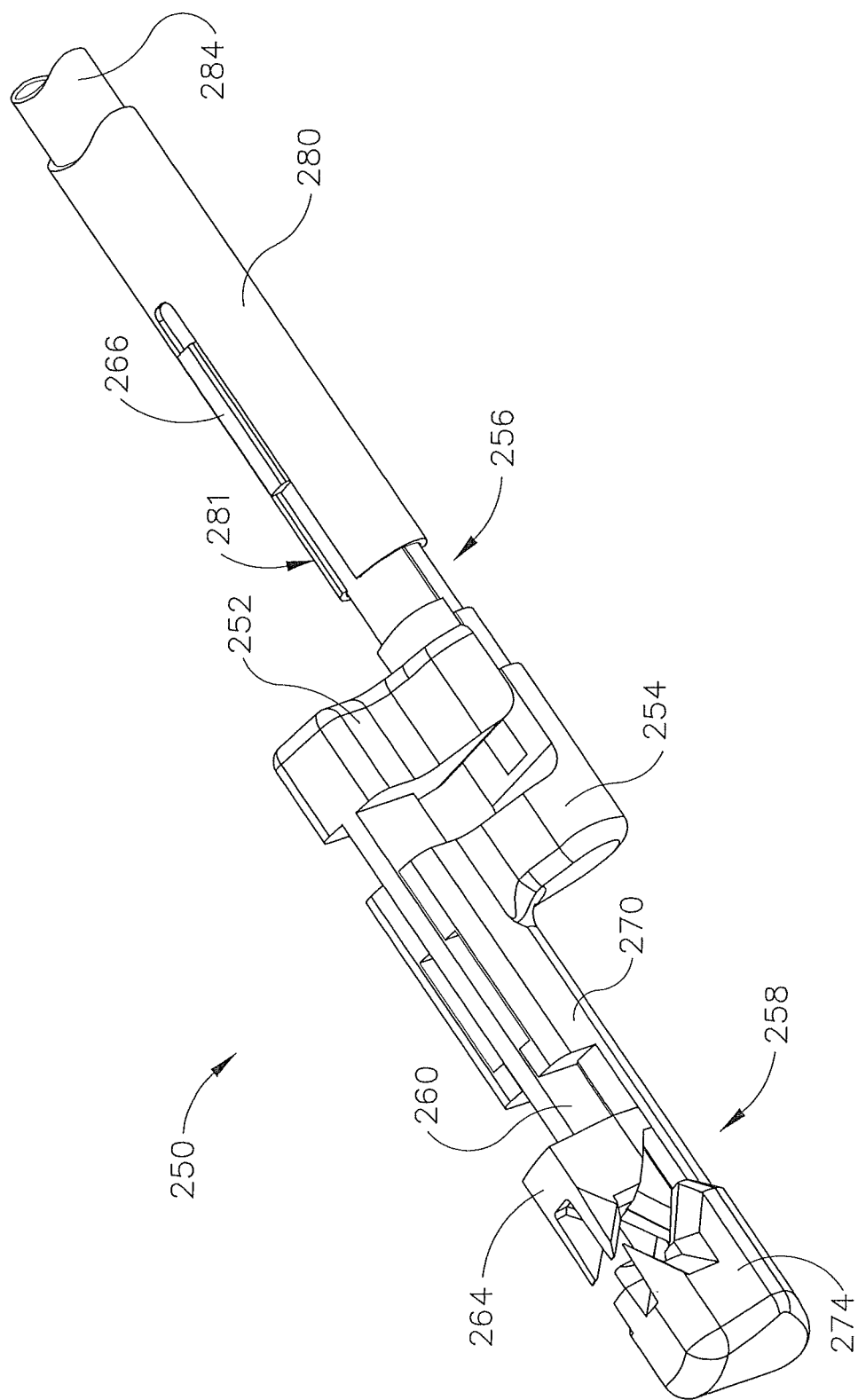
FIG. 8 depicts a first partial perspective view of a second needle grasping arm of the end effector of FIG. 3A.
Figure 9:
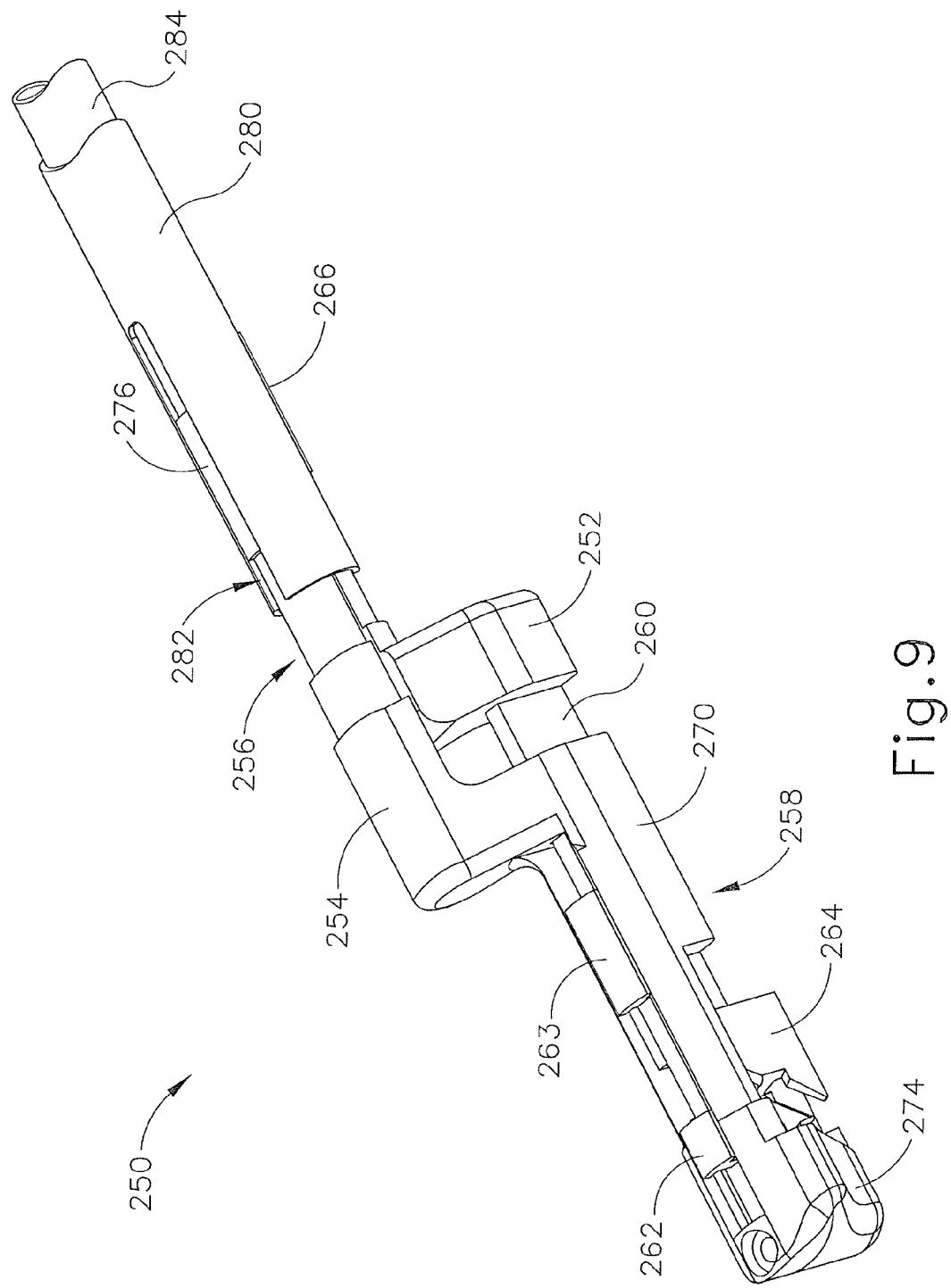
FIG. 9 depicts a second partial perspective view of the second needle grasping arm of FIG. 8.

FIG. 7 shows exemplary features that may be used to provide the simultaneous opposing motion of jaws (220, 230) described above. In particular, FIG. 7 shows a drive shaft (244) that includes a first threaded section (246) and a second threaded section (248). Drive shaft (244) is coaxially positioned within sheath (240) and is rotatable within sheath (240). Drive shaft (244) is rotatably driven by motor (28) in handle portion (20). The threading of first threaded section (246) is oriented opposite to the threading of second threaded section (248), such that threaded sections (246, 248) have opposite pitches. The proximal portions of jaws (220, 230) together encompass the distal portion of drive shaft (244). In particular, the proximal portion of jaw (220) includes threading (228) that meshes with first threaded section (246); while the proximal portion of jaw (230) includes threading (238) that meshes with second threaded section (248). It should therefore be understood that threading (228) has a pitch that is opposite to the pitch of threading (238). It should also be understood that, due to the relationships and orientations of threaded sections (246, 248) and threading (228, 238), drive shaft (244) will cause jaws (220, 230) to simultaneously translate away from each other (FIG. 6A) when drive shaft (244) is rotated in one direction; while drive shaft (244) will cause jaws (220, 230) to simultaneously translate toward each other (FIG. 6B) when drive shaft (244) is rotated in the other direction.

It should be understood that the opposing thread configuration described above may require relatively low torsional force to rotate drive shaft (244) to drive jaws (220, 230) toward and away from each other. It should also be understood that the opposing thread configuration described above may provide a relatively high holding force. For instance, when needle grasping features (224, 234) are driven toward each other to secure needle (50) as shown in FIG. 6B, and needle (50) is off-plane for whatever reason (e.g., incidentally oriented slightly obliquely relative to the longitudinal axis of shaft (100), etc.), the needle holding forces at grasping features (224, 234) may be self-reinforcing due to opposing forces provided through the opposing thread configuration described above, providing a mechanical advantage to urge needle (50) back into the desired planar orientation, even if tissue or some other structure is resisting such movement of needle into the desired planar orientation. Similarly, the opposing thread configuration described above may provide friction that acts as an anti-backup feature, substantially resisting inadvertent separation of grasping features (224, 234), thereby providing a very secure hold of needle (50). Other suitable components that may be used to provide opposing motion of grasping features (224, 234) (e.g., a pinion with opposing racks, etc.) will be apparent to those of ordinary skill in the art in view of the teachings herein.

As noted above, drive shaft (244) may be selectively driven in either rotational direction by motor (28), such as in response to actuation of rocker (24). Alternatively, any other motive source and/or user input feature may be used. It should also be understood that, while drive shaft (244) rotates about an axis that is parallel to the axis of shaft (100), alternative drive systems that include a rotary member may provide rotation of such a rotary member about an axis that is not parallel to the axis of shaft (100). For instance, a pinion based drive system may provide rotation of a drive pinion about an axis that is perpendicular to the axis of shaft (100). Other suitable ways in which jaws (220, 230) may be actuated will be apparent to those of ordinary skill in the art in view of the teachings herein.

B. Exemplary Second Grasping Arm

FIGS. 8-11 show second grasping arm (250) in greater detail. Second grasping arm (250) comprises a first jaw (260) and a second jaw (270). Jaws (260, 270) are substantially aligned with each other and are slidable longitudinally relative to each other. Jaw (260) includes a pair of flanges (262, 263) that are received through corresponding openings (272, 273) of jaw (270) during assembly of arm (250). Thereafter, flanges (262, 263) prevent jaws (260, 270) from deflecting transversely away from each other. Jaws (260, 270) also include complementary needle grasping features (264, 274) that are configured to selectively grasp needle (50) as will be described in greater detail below. The proximal portion of jaw (260) includes a transversely extending fin (266). Likewise, the proximal portion of jaw (270) also includes a transversely extending fin (276). Fins (266, 276) are slidably disposed in corresponding distal slots (281, 282) of a sheath (280), which will be described in greater detail below. Each jaw (260, 270)

of second grasping arm (250) includes a dogleg section (252, 254). Each dogleg section (252, 254) forms a pair of right angles between a proximal portion (256) of grasping arm (250) and a distal portion (258) of grasping arm (250). The configuration of dogleg sections (252, 254) provides distal portion (258) in a parallel yet offset position relative to proximal portion (256). Thus, when grasping arm (250) is rotated about a longitudinal axis extending along the length of the proximal portion (256) of grasping arm (250), the distal portion (258) of grasping arm (250) rotates in an orbital motion about that longitudinal axis. Such motion will be described in greater detail below.

Sheath (280) extends along the length of shaft (100) and is partially fixed within shaft (100). In particular, sheath (280) does not translate relative to shaft (100) in this example, though sheath (280) is rotatable relative to shaft (100). For instance, sheath (280) may be selectively rotated in either direction by motor (28) (e.g., in response to actuation of rocker (24), etc.). It should therefore be understood that rotation of sheath (280) relative to shaft (100) will provide rotation of second grasping arm (250) relative to shaft (100), due to the relationship between fins (266, 276) and slots (281, 282). As noted above, when second grasping arm (250) is rotated by sheath (280), the distal portion (258) of grasping arm (250) rotates in an orbital motion about the longitudinal axis that is defined by both sheath (280) and the proximal portion (256) of grasping arm (250). In some other versions, second grasping arm (250) is non-roatatable relative to shaft (100). It should also be understood that, in the present example, the relationship between fins (266, 276) and slots (281, 282) permits jaws (260, 270) to translate relative to sheath (280) and shaft (100).

Figure 10A:
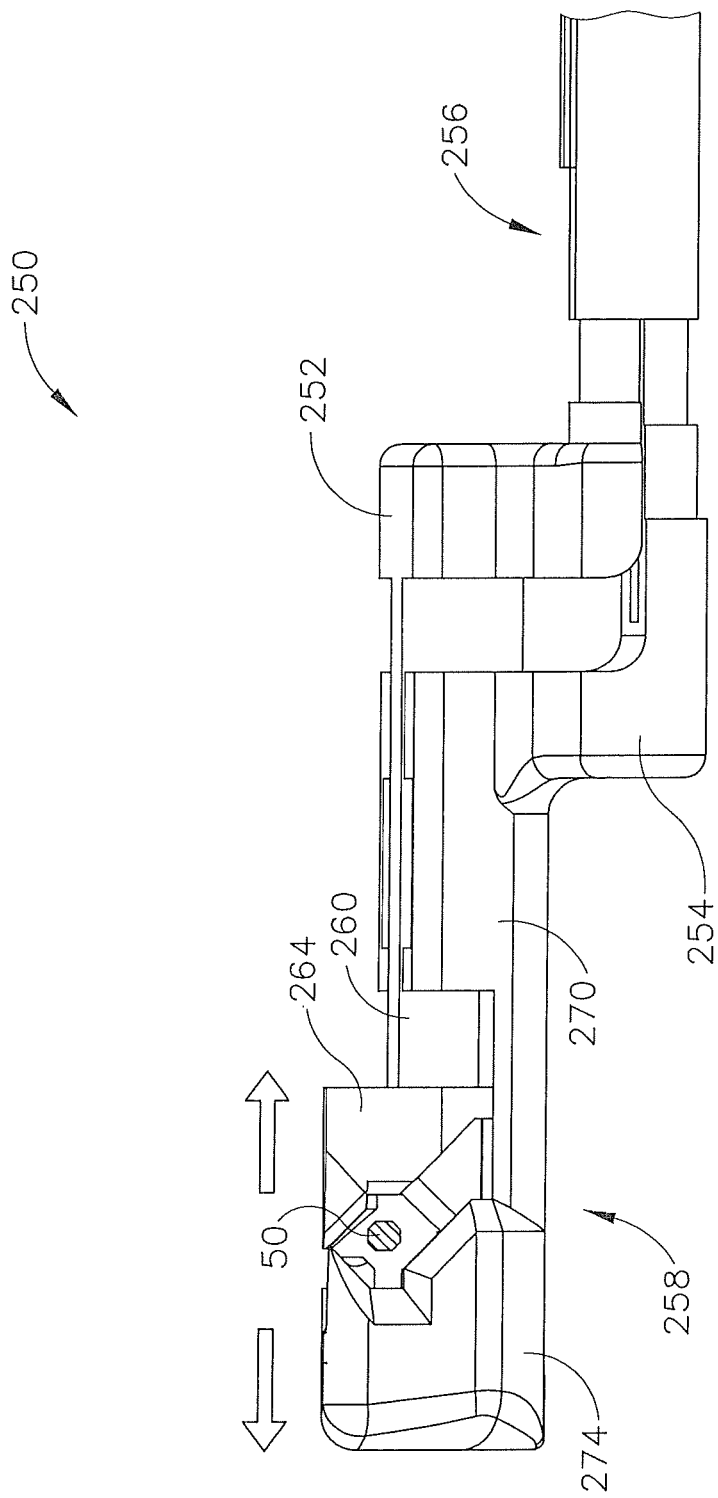
FIG. 10A depicts a partial side elevational view of the second needle grasping arm of FIG. 8, in a first operational configuration.
Figure 10B:
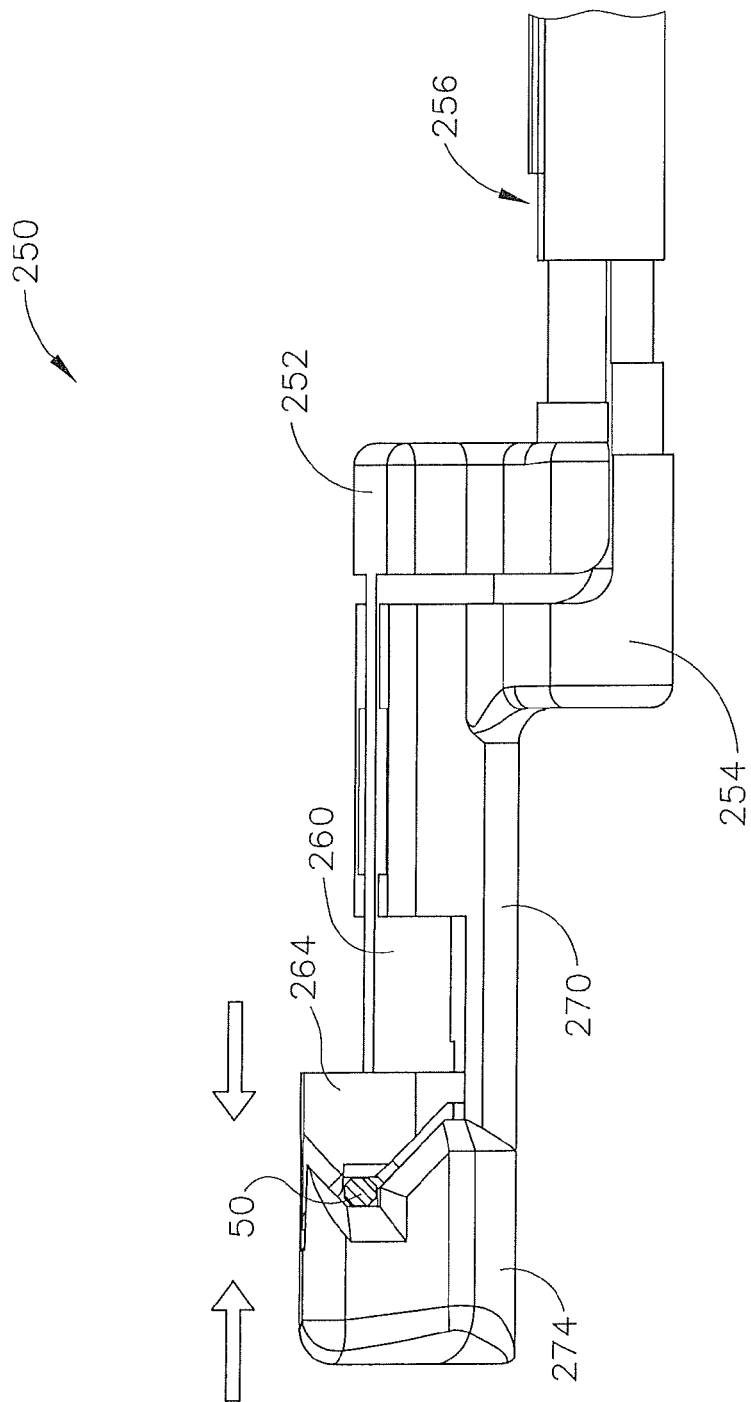
FIG. 10B depicts a partial side elevational view of the second needle grasping arm of FIG. 8, in a second operational configuration.

As best seen in FIGS. 10A-10B, jaws (260, 270) are simultaneously movable in opposite directions to selectively expand or reduce an opening formed by grasping features (264, 274) to receive needle (50). For instance, in FIG. 10A, jaw (260) has moved proximally toward shaft (100) and jaw (270) has simultaneously moved distally away from shaft (100) to enlarge the opening defined by grasping features (264, 274) to receive needle (50). In FIG. 10B, jaw (260) has moved distally away from shaft (100) and jaw (270) has simultaneously moved proximally toward shaft (100) to reduce the opening defined by grasping features (264, 274) to securely grasp needle (50). In some other versions, one jaw (260, 270) remains longitudinally stationary while the other jaw translates longitudinally to grasp or release needle (50) between grasping features (264, 274). However, it should be understood that in versions such as the present example where jaws (260, 270) both move simultaneously in opposite directions, such motion may further promote alignment of needle (50) within grasping features (264, 274) as compared to versions where one jaw (260, 270) always stays longitudinally fixed relative to shaft (100). In other words, having both grasping features (264, 274) always spaced equidistantly away from the intended path of needle (50) (regardless of whether jaws (260, 270) are open as shown in FIG. 10A or closed as shown in FIG. 10B) may better accommodate incidental deflections of needle (50) away from that intended path in either direction during use of instrument (10). Arm (250) may thus be particularly suited to accommodate instances where needle (50) has deviated away from the expected perpendicular plane of motion as described above.

Figure 11:
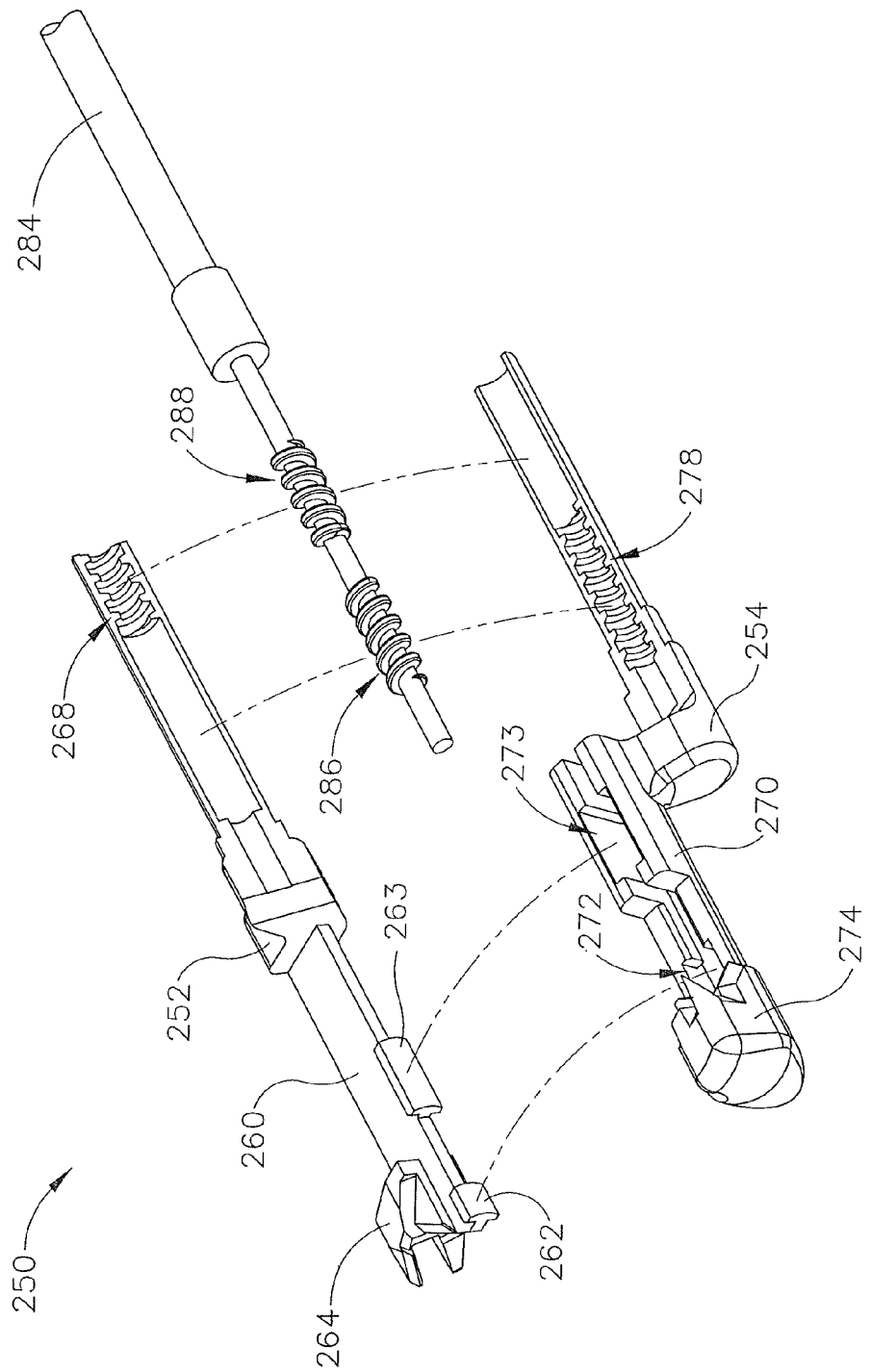
FIG. 11 depicts a partial exploded view of the second needle grasping arm of FIG. 8.

FIG. 11 shows exemplary features that may be used to provide the simultaneous opposing motion of jaws (260, 270) described above. In particular, FIG. 11 shows a drive shaft (284) that includes a first threaded section (286) and a second threaded section (288). Drive shaft (284) is coaxially positioned within sheath (280) and is rotatable within sheath (280). Drive shaft (284) is rotatably driven by motor (28) in handle portion (20). The threading of first threaded section (286) is oriented opposite to the threading of second threaded section (288), such that threaded sections (286, 288) have opposite pitches. The proximal portions of jaws (260, 270) together encompass the distal portion of drive shaft (284). In particular, the proximal portion of jaw (260) includes threading (268) that meshes with first threaded section (286); while the proximal portion of jaw (270) includes threading (278) that meshes with second threaded section (288). It should therefore be understood that threading (268) has a pitch that is opposite to the pitch of threading (278). It should also be understood that, due to the relationships and orientations of threaded sections (286, 288) and threading (268, 278), drive shaft (284) will cause jaws (260, 270) to simultaneously translate away from each other (FIG. 10A) when drive shaft (284) is rotated in one direction; while drive shaft (284) will cause jaws (260, 270) to simultaneously translate toward each other (FIG. 10B) when drive shaft (284) is rotated in the other direction.

In some settings, the rotational position of sheath (280) is fixed relative to shaft (100) when drive shaft (284) is rotated relative to shaft (100). Thus, sheath (280) substantially holds the rotational position of jaws (260, 270) when drive shaft (284) is rotated. In some other settings, sheath (280) and drive shaft (284) are rotated simultaneously relative to shaft (100). In some such instances, sheath (280) and drive shaft (284) are rotated in the same direction and at the same speed, such that drive shaft (284) and jaws (260, 270) are rotated in the same direction and at the same speed. Thus, the longitudinal positioning of jaws (260, 270) remains fixed during such rotation. As another merely illustrative variation, sheath (280) and drive shaft (284) may be rotated simultaneously relative to shaft (100), but at different speeds and/or in different directions. Such a scheme provides a rotation differential between jaws (260, 270) and drive shaft (284), such that jaws (260, 270) may open or close while second grasping arm (250) is simultaneously being rotated relative to shaft (100).

It should be understood that the opposing thread configuration described above may require relatively low torsional force to rotate drive shaft (284) to drive jaws (260, 270) toward and away from each other. It should also be understood that the opposing thread configuration described above may provide a relatively high holding force. For instance, when needle grasping features (264, 274) are driven toward each other to secure needle (50) as shown in FIG. 10B, and needle (50) is off-plane for whatever reason (e.g., incidentally oriented slightly obliquely relative to the longitudinal axis of shaft (100), etc.), the needle holding forces at grasping features (264, 274) may be self-reinforcing due to opposing forces provided through the opposing thread configuration described above, providing a mechanical advantage to urge needle (50) back into the desired planar orientation, even if tissue or some other structure is resisting such movement of needle into the desired planar orientation. Similarly, the opposing thread configuration described above may provide friction that acts as an anti-backup feature, substantially resisting inadvertent separation of grasping features (264, 274), thereby providing a very secure hold of needle (50). Other suitable components that may be used to provide opposing motion of grasping features (264, 274) (e.g., a pinion with opposing racks, etc.) will be apparent to those of ordinary skill in the art in view of the teachings herein.

As noted above, drive shaft (284) may be selectively driven in either rotational direction by motor (28), such as in response to actuation of rocker (24). Sheath (280) may also be driven by motor (28). Alternatively, any other motive source and/or user input feature may be used. It should also be understood that, while drive shaft (284) rotates about an axis that is parallel to the axis of shaft (100), alternative drive systems that include a rotary member may provide rotation of such a rotary member about an axis that is not parallel to the axis of shaft (100). For instance, a pinion based drive system may provide rotation of a drive pinion about an axis that is perpendicular to the axis of shaft (100). Other suitable ways in which one or more components of second grasping arm (250) may be actuated will be apparent to those of ordinary skill in the art in view of the teachings herein.

III. Exemplary Method of Operation

Figure 12A:
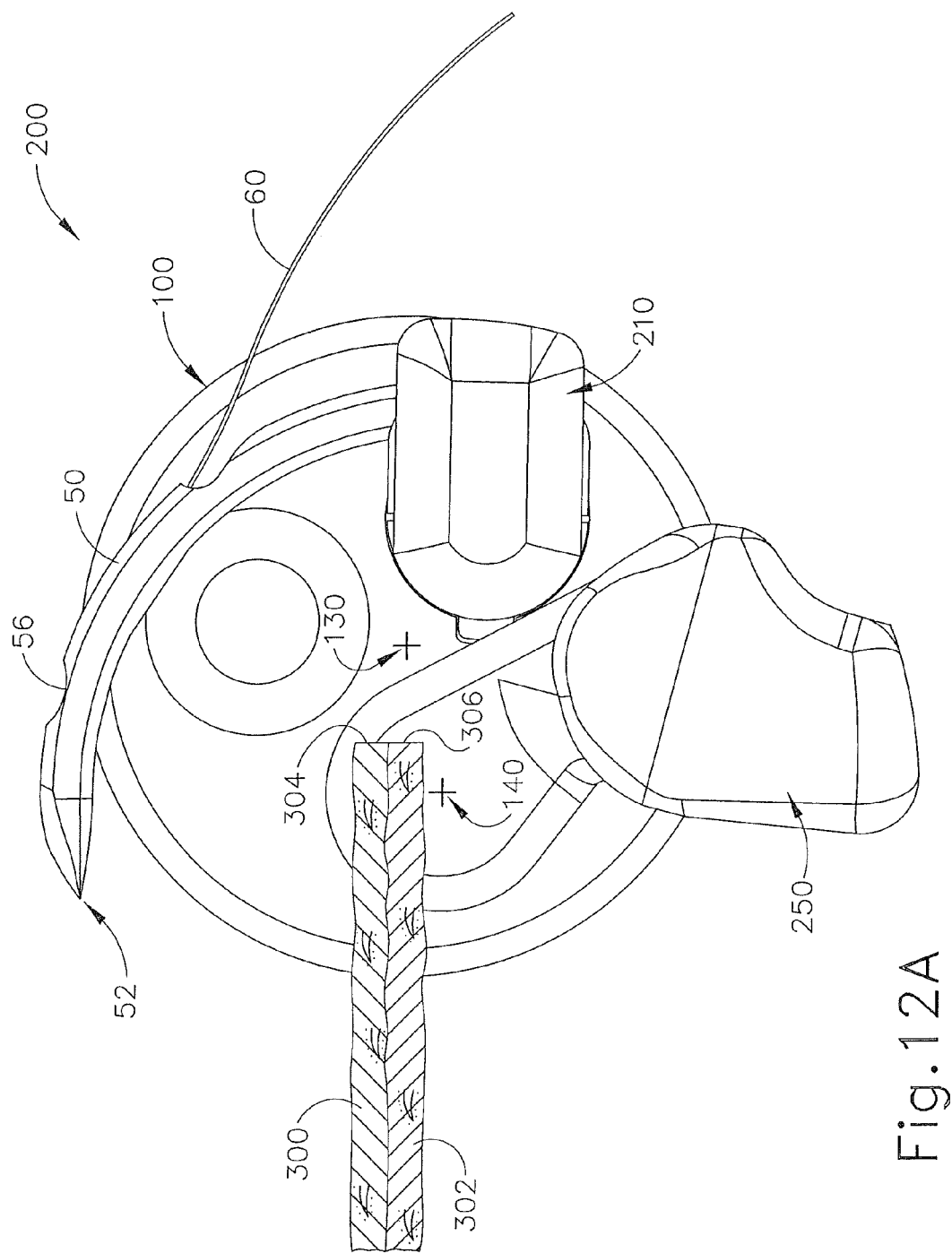
FIG. 12A depicts an end view of the end effector and needle of FIG. 3A, during an exemplary first stage of operation.

FIGS. 12A-12H depict a merely exemplary method for using surgical instrument (10). In particular, FIG. 12A shows end effector (200) positioned adjacent to apposed layers (300, 302) of tissue. End effector (200) is positioned such that the longitudinal axis (130) of shaft (100) is substantially parallel to the outer edges (304, 306) of tissue layers (300, 302). In this sense, "substantially parallel" simply means that end effector (200) is oriented in relation to tissue layers (300, 302) in a manner sufficient to enable needle (50) to be passed through tissue layers (300, 302). It should therefore be understood that longitudinal axis (130) need not necessarily be truly parallel with outer edges (304, 306), though longitudinal axis (130) may in fact be truly parallel with outer edges (304, 306) in some instances. It should also be understood that instrument (10) and needle (50) may be used to secure tissue together in an edge-to-edge arrangement rather than securing apposed layers (300, 302) as shown. Other suitable settings in which instrument (10) and needle (50) may be used will be apparent to those of ordinary skill in the art in view of the teachings herein. It should also be understood that the curved configuration of needle (50) may provide a more intuitive operation for the surgeon than a straight needle would, such as by providing better predictability for where sharp tip (52) will come through tissue.

Figure 12B:
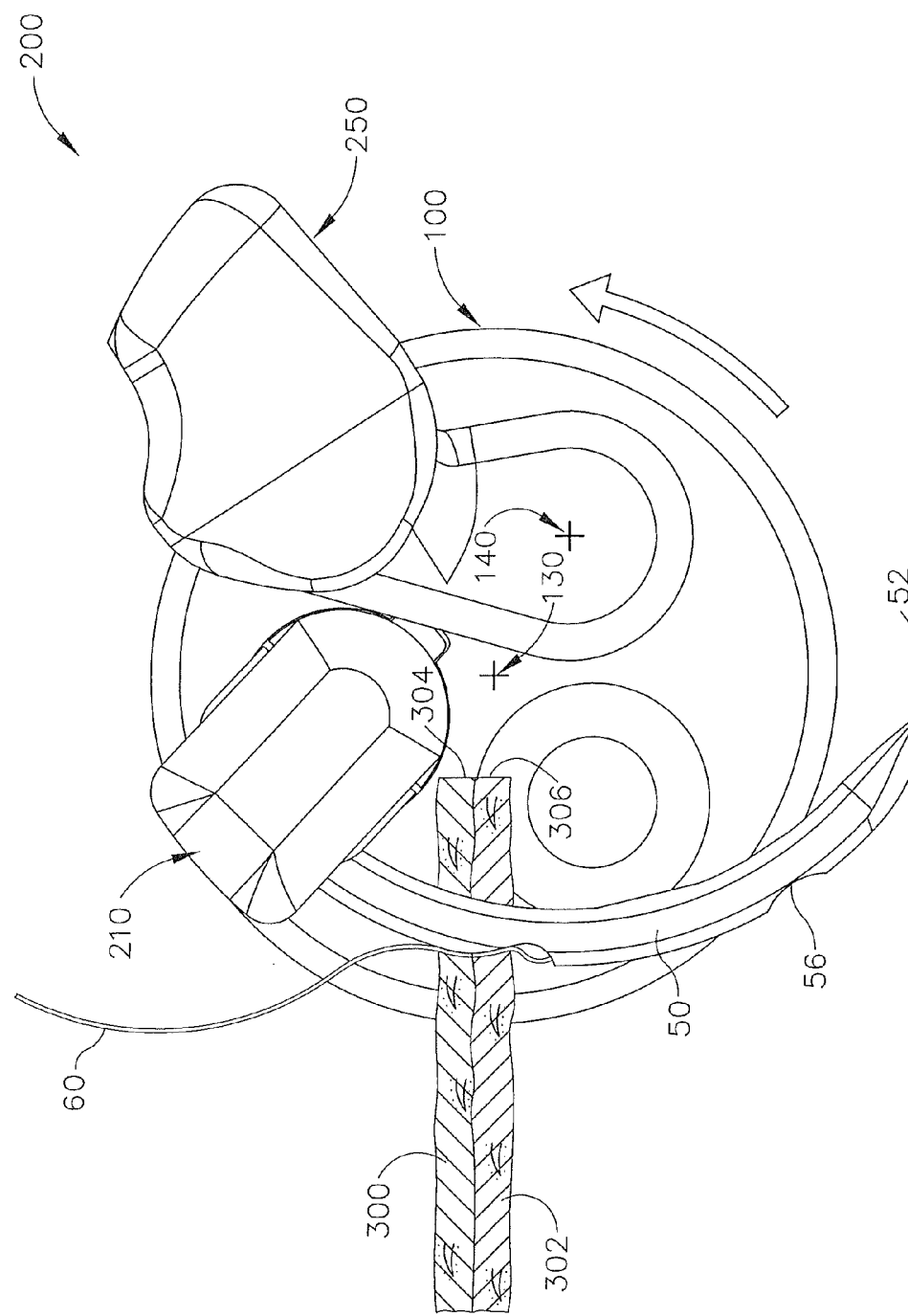
FIG. 12B depicts an end view of the end effector and needle of FIG. 3A, during an exemplary second stage of operation.

As shown in FIG. 12A, first grasping arm (210) is securely holding needle (50), with sharp tip (52) exposed. In particular, grasping portions (224, 234) of jaws (220, 230) hold needle (50) at grasping region (56). Needle (50) is oriented along a plane that is substantially transverse to longitudinal axis (130). Once end effector (200) has been positioned as shown in FIG. 12A, the entire instrument (10) is rotated about longitudinal axis (130) to drive sharp tip (52) through tissue layers (300, 302), as shown in FIG. 12B. In the example shown, the rotational direction for instrument (10) is counterclockwise viewed from the distal end toward the proximal end, though it should be understood that instrument (10) may be rotated clockwise instead (e.g., depending on the orientation of sharp tip (52)). During the transition from the position of FIG. 12A to the position of FIG. 12B, the rotational position of grasping arms (210, 250) relative to shaft (100) remains fixed, such that grasping arms (210, 250) rotate unitarily with shaft (100) about longitudinal axis (130). The longitudinal position of jaws (220, 230, 260, 270) also remains fixed during this transition. As can also be seen in FIG. 12B, needle (50) has started to pull suture (60) through tissue layers (300, 302) at this stage. It should be understood that, in the stages shown in FIGS. 12A-12B, grasping arms (210, 250) and needle (50) are in the same rotational positions relative to shaft (100) as shown in FIG. 3A. It should also be noted that the configuration of end effector (200) and needle (50) may provide the surgeon with enhanced visibility of sharp tip (52) exiting tissue layers (300, 302) during the transition from FIG. 12A to FIG. 12B, particularly with arm (250) being rotated out of the way at this stage.

Figure 12C:
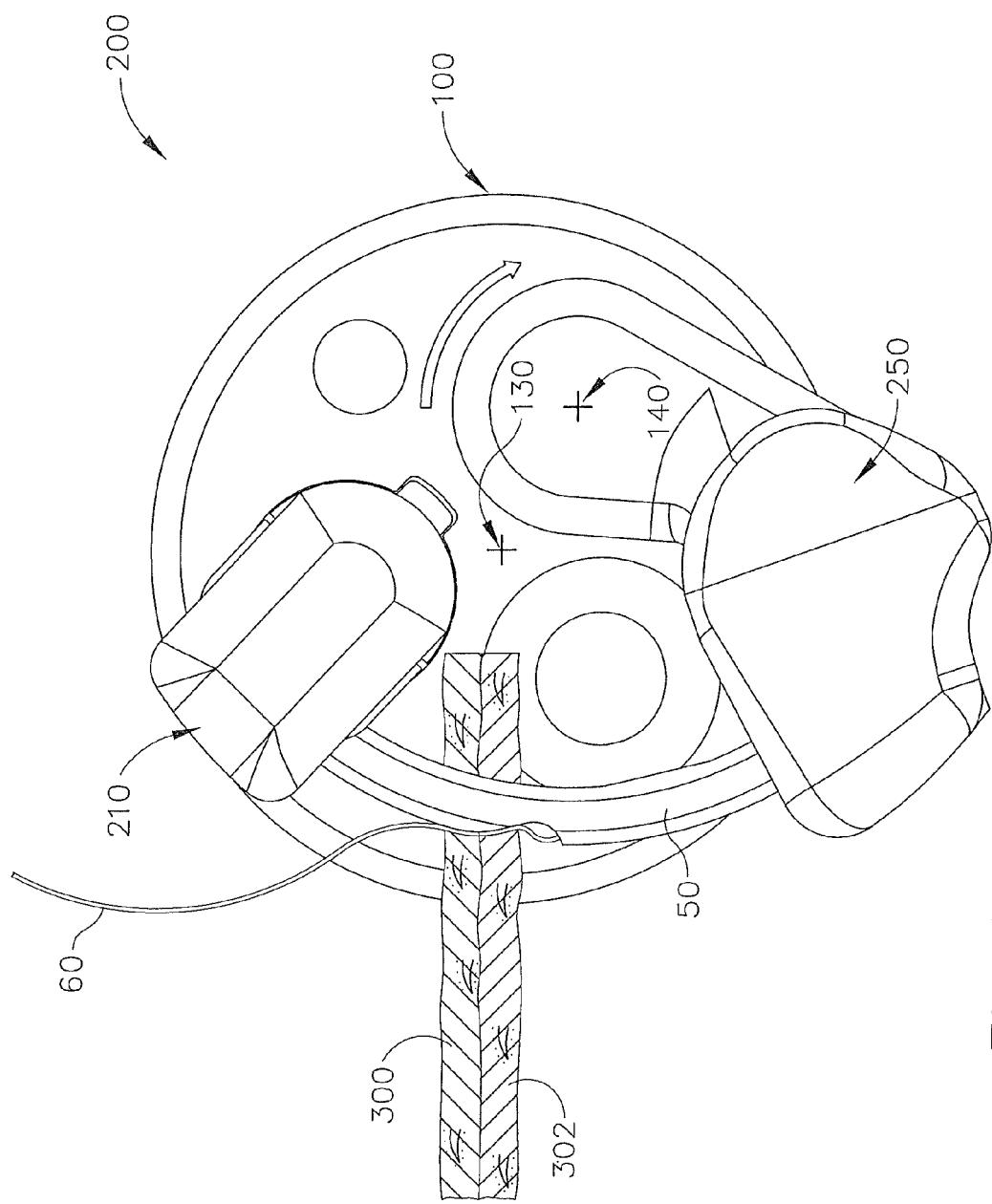
FIG. 12C depicts an end view of the end effector and needle of FIG. 3A, during an exemplary third stage of operation.

After needle (50) has been driven at least partially through tissue layers (300, 302), second grasping arm (250) is rotated about its own axis (140) toward needle (50) as shown in FIG. 12C. Such rotation is provided by rotating sheath (280) relative to shaft (100). The rotational position of shaft (100) relative to axis (130) remains fixed during the transition from the configuration shown in FIG. 12B to the configuration shown in FIG. 12C. It should be understood that, in the stage shown in FIG. 12C, grasping arms (210, 250) and needle (50) are in the same rotational positions relative to shaft (100) as shown in FIG. 3B.

In some versions, jaws (260, 270) are already opened (as shown in FIG. 10A) by the time second grasping arm (250) starts rotating from the position shown in FIG. 12B to the position shown in FIG. 12C. In some other versions, jaws (260, 270) are actively opened during the transition from the position shown in FIG. 12B to the position shown in FIG. 12C, such that jaws (260, 270) are fully open by the time second grasping arm (250) reaches the position shown in FIG. 12C. Once second grasping arm (250) reaches the position shown in FIG. 12C, jaws (260, 270) close (as shown in FIG. 10B) to grasp needle (50) at grasping region (58) with grasping features (264, 274). In addition, jaws (220, 230) open (as shown in FIG. 8A) to release needle (50) from grasping features (224, 234) at grasping region (56). In some versions, jaws (260, 270) close to grasp needle (50) at substantially the same time as jaws (220, 230) open to release needle (50). In some other versions, jaws (220, 230) do not open to release needle (50) until jaws (260, 270) have closed to grasp needle (50). Various suitable timing schemes and ways in which such schemes may be carried out will be apparent to those of ordinary skill in the art in view of the teachings herein.

Figure 12D:
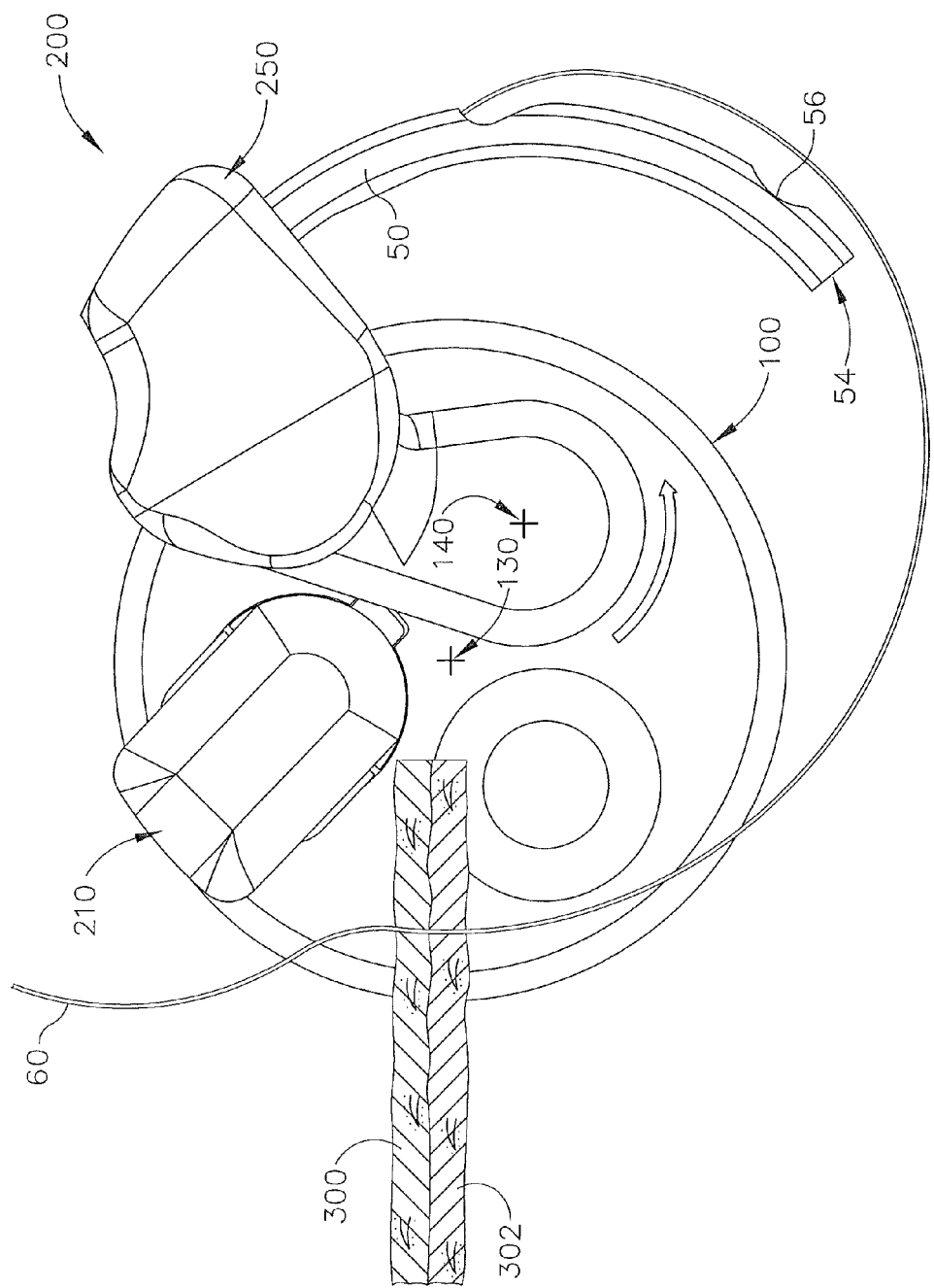
FIG. 12D depicts an end view of the end effector and needle of FIG. 3A, during an exemplary fourth stage of operation.

Once control of needle (50) has been effectively passed from grasping arm (210) to grasping arm (250), grasping arm (250) is rotated about axis (140) to the position shown in FIG. 12D. Such rotation is provided by once again rotating sheath (280) relative to shaft (100). The rotational position of shaft (100) relative to axis (130) continues to be fixed during the transition from the configuration shown in FIG. 12C to the configuration shown in FIG. 12D. It should be understood that, in the stage shown in FIG. 12D, grasping arms (210, 250) and needle (50) are in the same rotational positions relative to shaft (100) as shown in FIG. 3C. As can also be seen in FIG. 12D, grasping arm (250) pulls suture (60) through tissue layers (300, 302) during the transition from FIG. 12C to FIG. 12D.

Figure 12E:
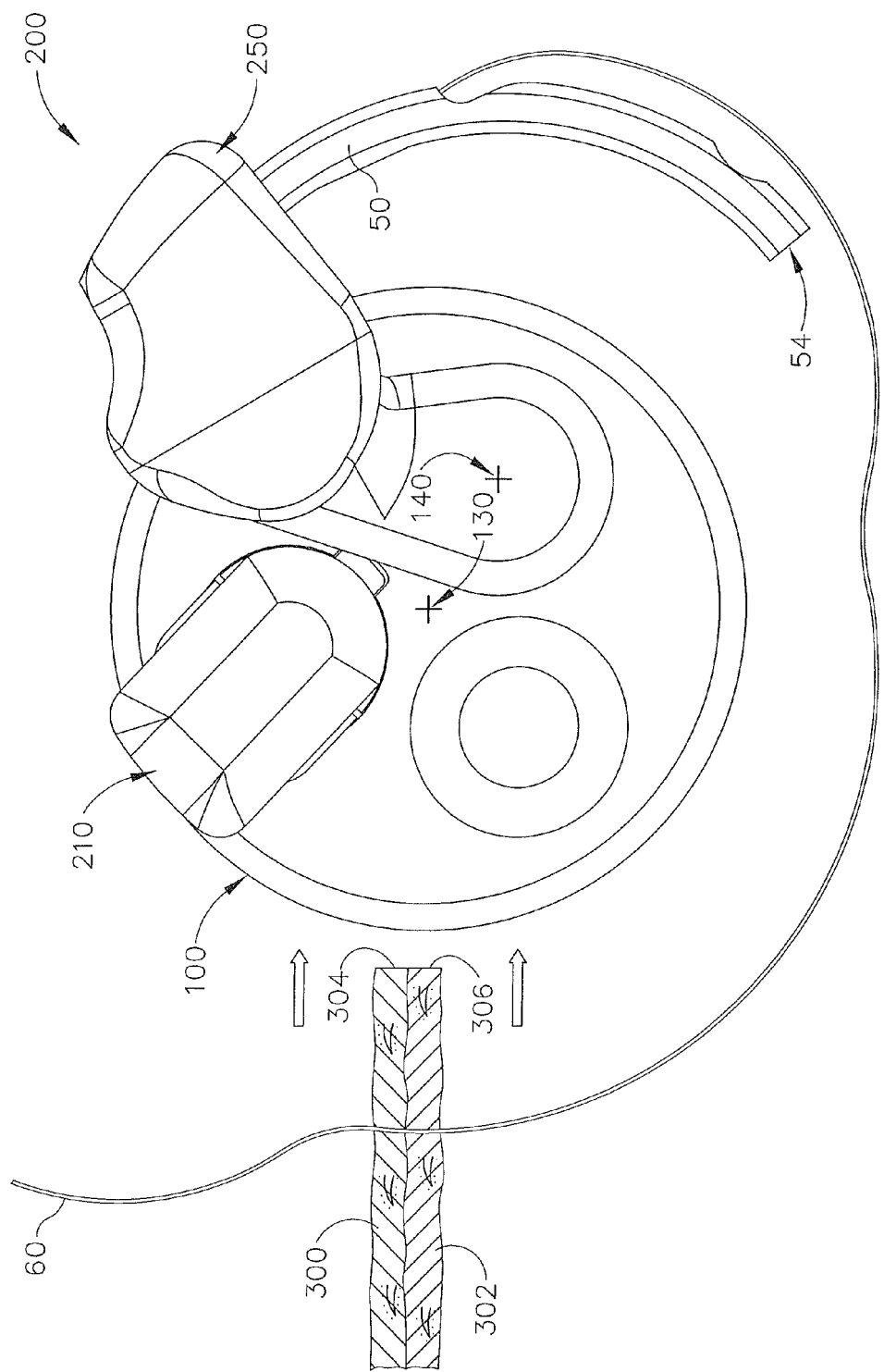
FIG. 12E depicts an end view of the end effector and needle of FIG. 3A, during an exemplary fifth stage of operation.

After reaching the configuration shown in FIG. 12D, the surgeon pulls the entire end effector (200) away from tissue layers (300, 302), along a path that is substantially transverse to axis (130), as shown in FIG. 12E. It should be understood that this path may be oblique relative to axis (130) and/or edges (304, 306), helical, and/or of any other suitable configuration. It should also be understood that neither arm (210, 250) is rotated relative to shaft (100) in the present example during the transition from the position shown in FIG. 12D to the position shown in FIG. 12E. Thus, in the stage shown in FIG. 12E, grasping arms (210, 250) and needle (50) are still in the same rotational positions relative to shaft (100) as shown in FIG. 3C. In moving instrument (10) away from tissue layers (300, 302) during the transition to the position shown in FIG. 12E, suture (60) is pulled further through tissue layers (300, 302).

Figure 12F:
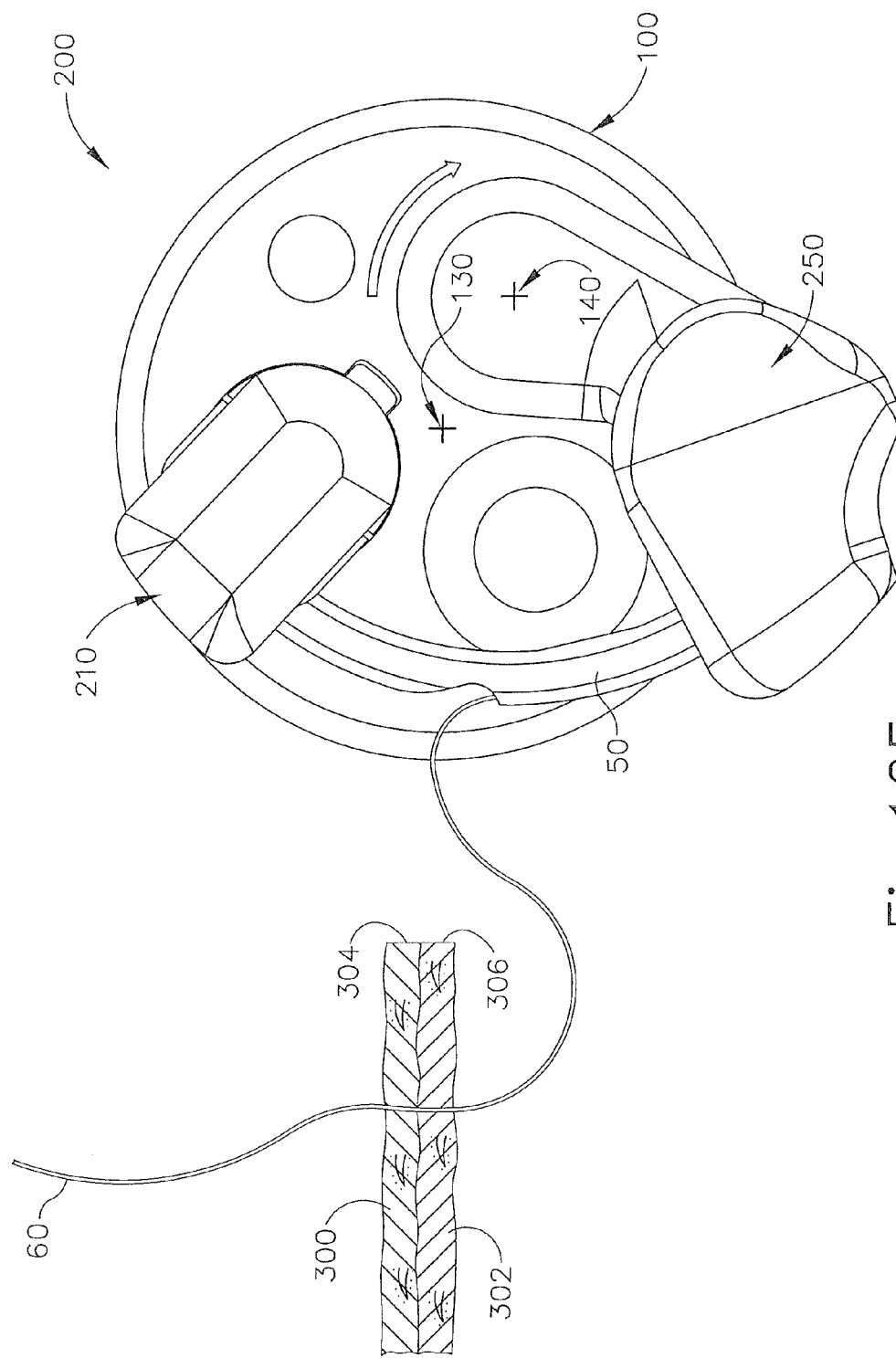
FIG. 12F depicts an end view of the end effector and needle of FIG. 3A, during an exemplary sixth stage of operation.

With end effector (200) positioned sufficiently away from tissue layers (300, 302), second grasping arm (250) is rotated about axis (140) to the position shown in FIG. 12F. The rotational position of shaft (100) relative to axis (130) remains fixed during the transition from the configuration shown in FIG. 12E to the configuration shown in FIG. 12F. It should be understood that, in the stage shown in FIG. 12F, grasping arms (210, 250) and needle (50) are in the same rotational positions relative to shaft (100) as shown in FIG. 3B. End effector (200) is positioned far enough away from tissue layers (300, 302) during the transition from the position shown in FIG. 12E to the position shown in FIG. 12F such that blunt end (54) of needle (50) does not touch tissue layers (300, 302). The rotation of second grasping arm (250) to the position shown in FIG. 12F places grasping region (58) of needle (50) back between grasping portions (224, 234) of jaws (220, 230).

In some versions, jaws (220, 230) are already opened (as shown in FIG. 8A) by the time second grasping arm (250) starts rotating from the position shown in FIG. 12E to the position shown in FIG. 12F. In some other versions, jaws (220, 230) are actively opened during the transition from the position shown in FIG. 12E to the position shown in FIG. 12F, such that jaws (220, 230) are fully open by the time second grasping arm (250) reaches the position shown in FIG. 12F. Once second grasping arm (250) reaches the position shown in FIG. 12F, jaws (220, 230) close (as shown in FIG. 8B) to grasp needle (50) at grasping region (56) with grasping portions (224, 234). In addition, jaws (260, 270) open (as shown in FIG. 10A) to release needle (50) from grasping portions (264, 274) at grasping region (58). In some versions, jaws (220, 230) close to grasp needle (50) at substantially the same time as jaws (260, 270) open to release needle (50). In some other versions, jaws (260, 270) do not open to release needle (50) until jaws (220, 240) have closed to grasp needle (50). Various suitable timing schemes and ways in which such schemes may be carried out will be apparent to those of ordinary skill in the art in view of the teachings herein.

Once control of needle (50) has been effectively passed from grasping arm (250) back to grasping arm (210), grasping arm (250) is rotated about axis (140) to the position shown in FIG. 12G. Such rotation is provided by once again rotating sheath (280) relative to shaft (100). The rotational position of shaft (100) relative to axis (130) continues to be fixed during the transition from the position shown in FIG. 12F to the position shown in FIG. 12G. It should be understood that, in the stage shown in FIG. 12G, grasping arms (210, 250) and needle (50) are in the same rotational positions relative to shaft (100) as shown in FIG. 3A.

Figure 12H:
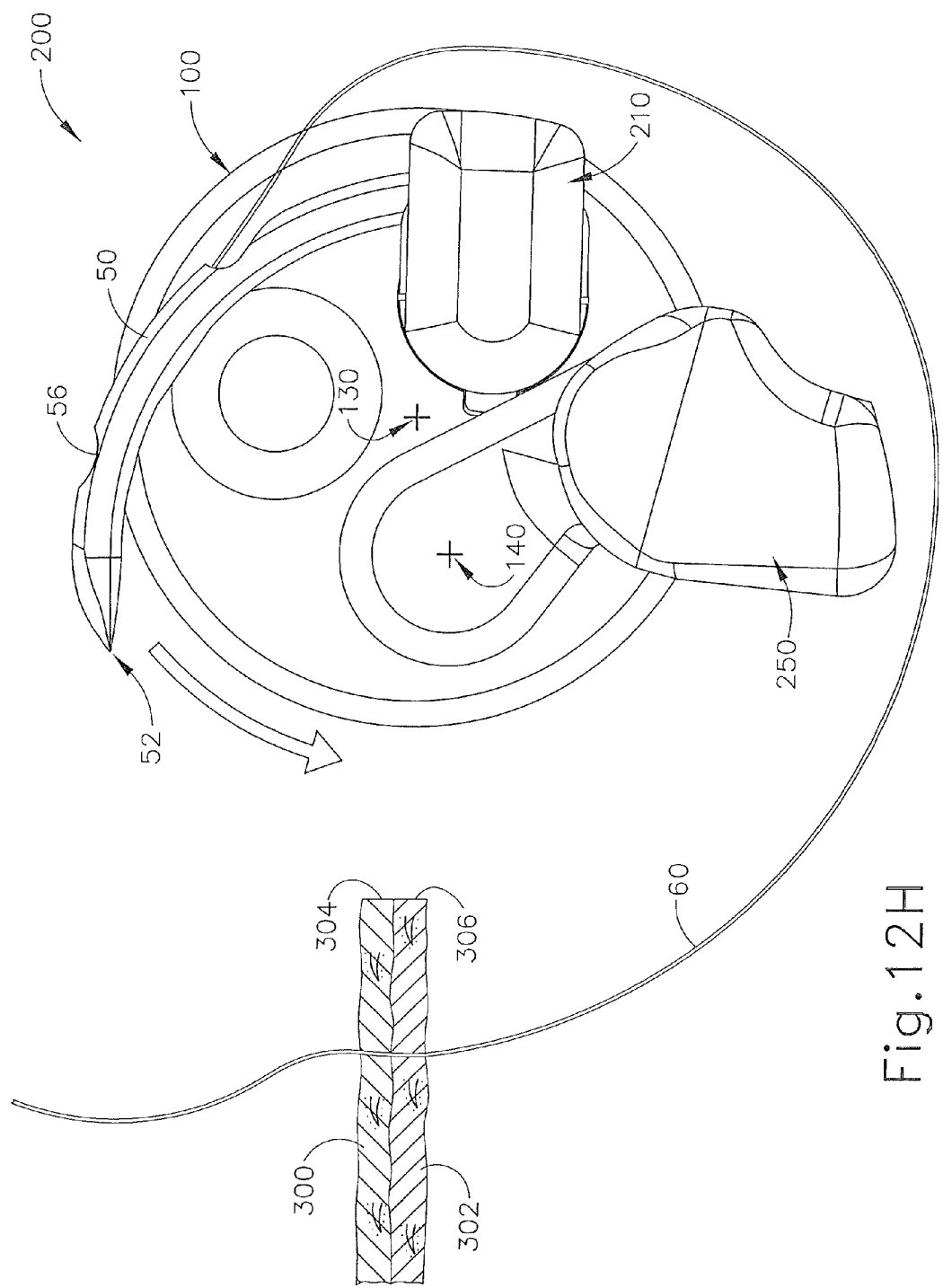
FIG. 12H depicts an end view of the end effector and needle of FIG. 3A, during an exemplary eighth stage of operation.

Once grasping arm (250) has been rotated away from needle (50) as shown in FIG. 12G, the entire instrument (10) is once again rotated about longitudinal axis (130) to position sharp tip (52) above tissue layers (300, 302), as shown in FIG. 12H. In the example shown, the rotational direction for instrument (10) is again counterclockwise viewed from the distal end toward the proximal end, though it should be understood that instrument (10) may be rotated clockwise instead (e.g., depending on the orientation of sharp tip (52)). During this transition, the rotational position of grasping arms (210, 250) relative to shaft (100) remains fixed, such that grasping arms (210, 250) rotate unitarily with shaft (100) about longitudinal axis (130). The longitudinal position of jaws (220, 230, 260, 270) also remains fixed during this transition. In the stage shown in FIG. 12H, grasping arms (210, 250) and needle (50) remain in the same rotational positions relative to shaft (100) as shown in FIG. 3A.

Having reached the configuration shown in FIG. 12H, end effector (200) may be moved back toward tissue layers (300, 302), such as along a path transverse to axis (130), to again reach the position shown in FIG. 12A. The above described cycle may then be repeated as many times as desired until an appropriate number of stitches have been made through tissue layers (300, 302). The free end of suture (50) may then be knotted, clipped, or otherwise secured.

It should be understood that instrument (10) may be advanced distally or proximally along axis (130) in each stitching cycle, each stitching cycle being represented by the succession of stages depicted in FIGS. 12A-12H. For instance, instrument (10) may be advanced distally or proximally along axis (130) during the transition from the position shown in 12E to the position shown in 12F. As another merely illustrative example, instrument (10) may be advanced distally or proximally along axis (130) during the transition from the position shown in 12G to the position shown in 12H. Other suitable stages at which instrument (10) may be advanced distally or proximally will be apparent to those of ordinary skill in the art in view of the teachings herein. It should be understood that the distance of each incremental distal or proximal movement of instrument (10) during successive stitching cycles may be selected based on a desired stitch density along the length of the tissue being sutured. It should also be understood that, once stitching is complete, suture (60) may define a generally helical path through tissue layers (300, 302). Other suitable ways in which instrument (10) may be used will be apparent to those of ordinary skill in the art in view of the teachings herein.

As should be apparent to those of ordinary skill in the art, needle (50) of the present example orbits about axis (140), which is offset from axis (130) of shaft (100) in the present example. This may enable needle (50) to travel about an arc having a radius that is greater than the radius of a trocar through which shaft (100) is inserted. In other words, the circumferential path of needle (50) need not be limited to the circumference of the trocar through which shaft (100) is inserted when the orbital axis of needle (50) is offset from axis (130) of shaft (100). Thus, the configuration of end effector (200) in the present example may permit a larger radius needle to be used, and larger stitches to be made, than what would be permitted if the orbital motion of needle (50) were centered about axis (130) of shaft (100). In some other versions, needle (50) does move in an orbital fashion about axis (130) of shaft (100).

IV. Exemplary Alternative End Effector

FIGS. 13A-13D depict an exemplary alternative end effector (400) disposed at the distal end of a shaft (500). End effector (400) of this example comprises a first arm (410) and a second arm (450). Either or both arms (410, 450) may be driven by a motor, manual mechanism, and/or some other feature. First arm (410) includes a needle grasping feature (412) and a dogleg section (414). Second arm (450) includes a needle grasping feature (462) and a dogleg section (464). Needle grasping features (412, 462) are each operable to selectively grasp and release a needle (600). Various suitable components and configurations for needle grasping features (412, 462) will be apparent to those of ordinary skill in the art in view of the teachings herein. Dogleg sections (414, 464) are configured such that the distal portions of arms (410, 450) are spaced apart to a distance exceeding the outer diameter of shaft (500). Each arm (410, 450) is independently rotatable about its own respective axis, relative to shaft (500). In some other versions, only one arm (410, 450) is rotatable relative to shaft (500) while the rotational position of the other arm (450) remains fixed relative to shaft (500).

Needle (600) of this example includes a first sharp tip (602) and a second sharp tip (604). A suture (610) is secured to a mid-region of needle (600). Needle (600) may be constructed in accordance with various teachings above and/or in accordance with at least some of the teachings of one or more of the references that are cited herein. Various suitable configurations for needle (600) will be apparent to those of ordinary skill in the art.

Figure 13A:
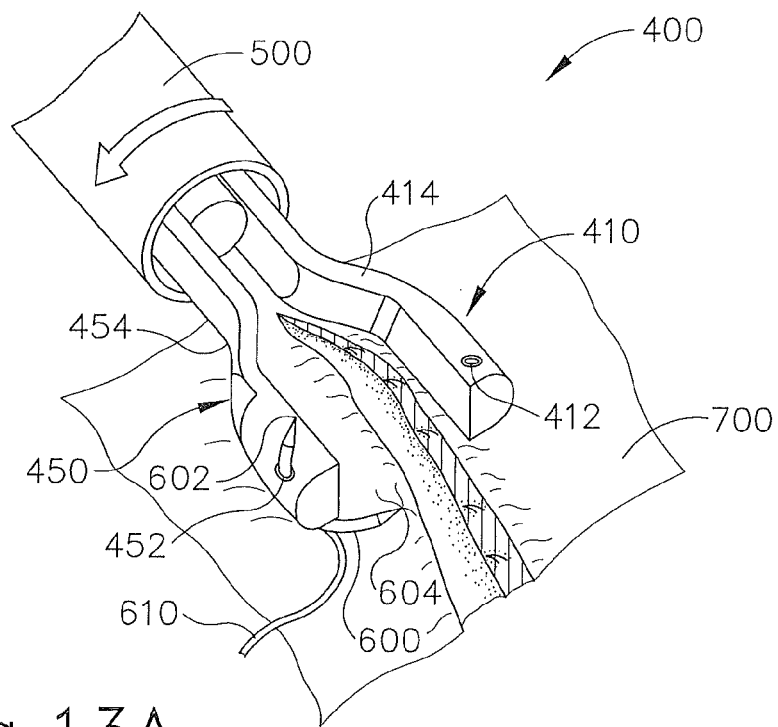
FIG. 13A depicts a partial perspective view of an exemplary alternative end effector, during an exemplary first stage of operation.
Figure 13B:
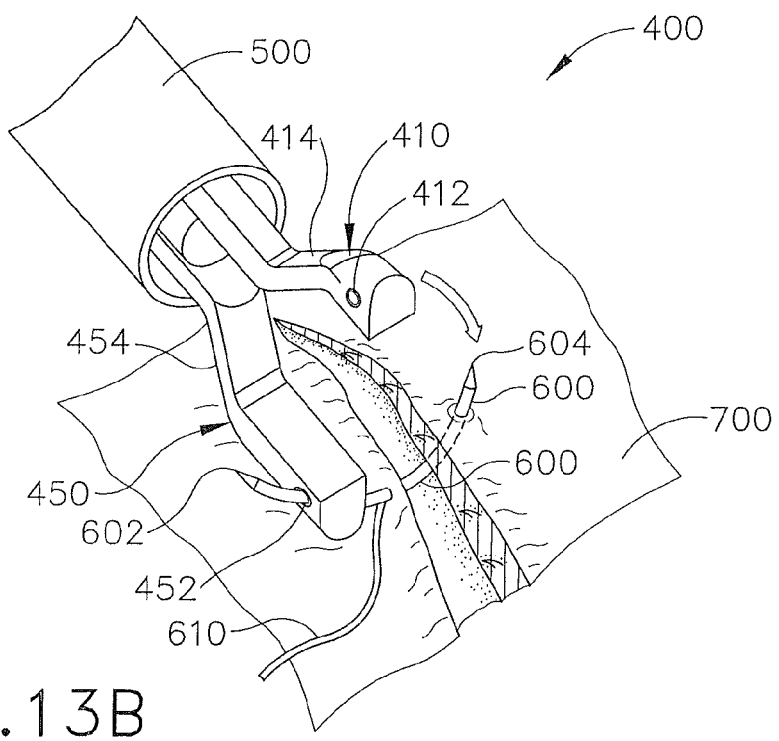
FIG. 13B depicts a partial perspective view of the end effector of FIG. 13A, during an exemplary second stage of operation.
Figure 13C:
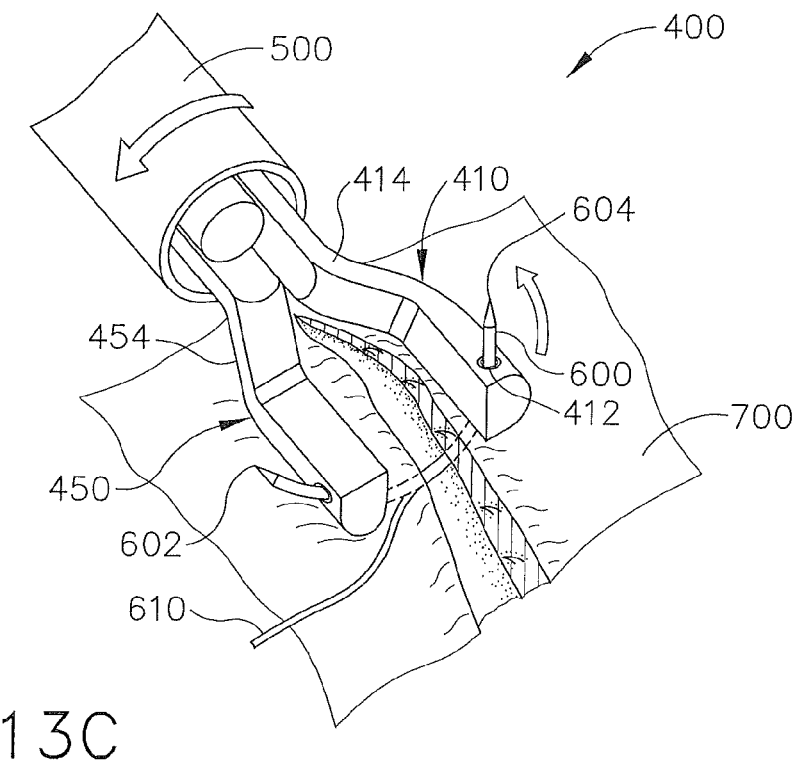
FIG. 13C depicts a partial perspective view of the end effector of FIG. 13A, during an exemplary third stage of operation.

In a merely exemplary use of end effector (400) and needle (600), end effector (400) and needle (600) are positioned with sharp tip (604) adjacent to tissue (700) as shown in FIG. 13A. Then, the entire assembly of shaft (400) and end effector (400) is rotated approximately 90° counterclockwise to the position shown in FIG. 13B. The positions of arms (410, 450) remain substantially fixed relative to shaft (500) during this transition. As can be seen in FIG. 13B, sharp tip (604) is driven through tissue (700) during the transition from FIG. 13A to FIG. 13B. Next, arm (410) is rotated clockwise toward sharp tip (604) to the position shown in FIG. 13C. The rotational position of shaft (500) and arm (450) remain substantially fixed during this transition. With arm (410) at the position shown in FIG. 13C, grasping feature (412) grasps needle (600) and grasping feature (452) releases needle (600). As described above, this grasping and releasing may occur in stages and/or simultaneously.

Figure 13D:
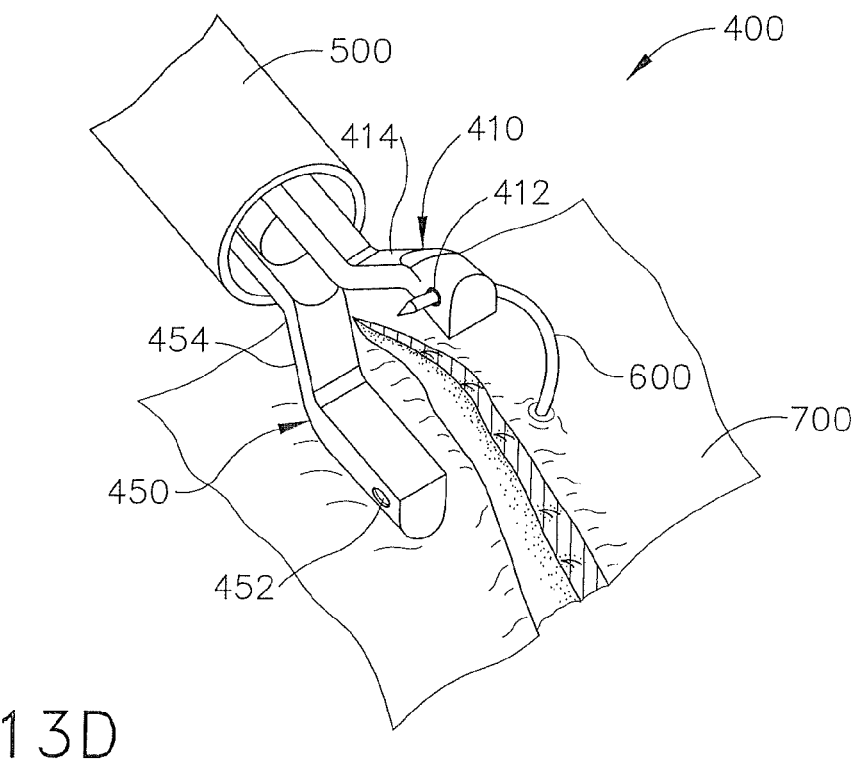
FIG. 13D depicts a partial perspective view of the end effector of FIG. 13A, during an exemplary fourth stage of operation.

Once control of needle (600) has been effectively passed from arm (450) to arm (410), arm (410) is rotated counterclockwise to the position shown in FIG. 13D. The rotational position of shaft (500) and arm (450) remain substantially fixed during this transition. The movement of arm (410) from the position shown in FIG. 13C to the position shown in FIG. 13D pulls needle (600) and suture (610) through tissue (700). At this stage, arm (410) may continue to rotate counterclockwise relative to shaft (500) until tip (602) clears tissue (700). Alternatively, shaft (500) and the entire end effector (400) may be rotated counterclockwise until tip (602) clears tissue (700). Next, there are at least two options for further operation. One option is to pull shaft (500) and end effector (400) transversely away from tissue (700); then pass needle (600) back to arm (450) while needle (600) is away from tissue (700), to repeat the process beginning back at the type of stage shown in FIG. 13A. Another option is to simply advance shaft (500) and end effector (400) distally or proximally; then to rotate either arm (410) or the entire assembly of shaft (500) and end effector (400) to drive tip (602) back through tissue (700). After tip (602) is driven back through tissue (700), arm (450) may take control of needle (600) from arm (410), and the process may be repeated beginning back at the type of stage shown in FIG. 13A. Still other suitable ways in which end effector (400) and needle (600) may be used will be apparent to those of ordinary skill in the art in view of the teachings herein.

In some variations, needle (600) includes graduations facilitating selective gripping of needle (600) at different locations along the length of needle (600), allowing more or less of each end of needle (600) to be exposed relative to each arm (410, 450). In addition or in the alternative, a taper at each end of needle (600) may prevent needle (600) from being passed too far through each needle grasping feature (412, 462).

While terms such as "clockwise" and "counterclockwise" have been used to describe directions of rotational movement during exemplary uses of end effectors (200, 400), it should be understood that these specific rotational directions are being provided only in reference to the examples depicted in the drawings. It is contemplated that rotational movement may be provided in directions opposite to those used above. Therefore, use of the terms "clockwise" and "counterclockwise" in the above examples should not be viewed as limiting in any way.

V. Miscellaneous

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a shaft, wherein the shaft has a distal end, wherein the shaft further has a radius and defines a central longitudinal axis; and
   (b) an end effector located at the distal end of the shaft, wherein the end effector comprises:
      (i) a first needle grasping arm, wherein the first needle grasping arm is operable to selectively grasp and release a suture needle, wherein the first needle grasping arm extends along a first arm axis, wherein the first arm axis is parallel to the central longitudinal axis; and
      (ii) a second needle grasping arm, wherein the second needle grasping arm is operable to selectively grasp and release a suture needle, wherein the second needle grasping arm extends along a second arm axis, wherein the second arm axis is parallel to the central longitudinal axis,
      wherein the first and second needle grasping arms are operable to drive a suture needle along a rotational path about an axis that is parallel to and offset from the central longitudinal axis of the shaft, wherein the first needle grasping arm is operable to drive the suture needle along a first portion of the rotational path having a first radius, and wherein the second needle grasping arm is operable to drive the suture needle along a second portion of the rotational path having a second radius different than the first radius.

2. The apparatus of claim 1, wherein the first arm axis is offset from the central longitudinal axis of the shaft.

3. The apparatus of claim 2, wherein the second arm axis is offset from the central longitudinal axis of the shaft.

4. The apparatus of claim 2, wherein the first and second needle grasping arms are operable to drive a suture needle along a rotational path about the second arm axis.

5. The apparatus of claim 1, wherein the axis of the rotational path along which the first and second grasping arms are operable to drive a suture needle is parallel to the central longitudinal axis of the shaft, such that the rotational path is perpendicular to the central longitudinal axis of the shaft.

6. The apparatus of claim 1, wherein the rotational path has a radius greater than the radius of the shaft.

7. The apparatus of claim 1, wherein the second needle grasping arm comprises a proximal section, a dogleg section, and a distal section, wherein the proximal section extends along the second arm axis, wherein the distal section extends along an axis that is offset from the second arm axis.

8. The apparatus of claim 7, wherein the axis of the distal section is parallel to the second arm axis.

9. The apparatus of claim 1, wherein the first needle grasping arm is substantially straight.

10. The apparatus of claim 1, wherein the second needle grasping arm is rotatable relative to the shaft about the first arm axis.

11. The apparatus of claim 10, wherein the first needle grasping arm is not rotatable relative to the shaft.

12. The apparatus of claim 1, wherein the first needle grasping arm comprises a pair of opposing jaws, wherein the second needle grasping arm comprises a pair of opposing jaws.

13. The apparatus of claim 1, wherein the shaft and the end effector are dimensioned to fit through a surgical trocar.

14. The apparatus of claim 1, further comprising a handle assembly positioned at a proximal end of the shaft, wherein the handle assembly is operable to selectively activate the end effector.

15. The apparatus of claim 14, wherein the handle assembly further includes at least one motor in communication with the end effector.

16. An apparatus, comprising:
   (a) a shaft, wherein the shaft has a distal end, wherein the shaft further has a radius and defines a central longitudinal axis; and
   (b) an end effector located at the distal end of the shaft, wherein the end effector comprises:
      (i) a first needle grasping arm, wherein the first needle grasping arm is operable to selectively grasp and release a suture needle, wherein the first needle grasping arm extends along a first arm axis, wherein the first arm axis is parallel to and offset from the central longitudinal axis of the shaft, and
      (ii) a second needle grasping arm, wherein the second needle grasping arm is operable to selectively grasp and release a suture needle, wherein the second needle grasping arm extends along a second arm axis, wherein the second arm axis is parallel to and offset from the central longitudinal axis of the shaft,
      wherein the first and second needle grasping arms are operable to drive a suture needle along a rotational path about an axis parallel to and offset from the central longitudinal axis, the first arm axis, and the second arm axis, wherein the first needle grasping arm is configured to drive the suture needle along a first portion of the rotational path having a first radius, wherein the second needle grasping arm drives the suture needle along a second portion of the rotational path having a second radius, and wherein the second radius is greater than the first radius.

17. The apparatus of claim 16, wherein the rotational path along which the first and second needle grasping arms are operable to drive a suture needle is about an axis that is offset from the central longitudinal axis of the shaft.

18. The apparatus of claim 16, wherein one or both of:
   (i) the first needle grasping arm is rotatable about the first arm axis, or
   (ii) the second needle grasping arm is rotatable about the second arm axis.

* * * * *